United States Patent [19]

Hajos et al.

[11] Patent Number: 5,021,574

[45] Date of Patent: * Jun. 4, 1991

[54] 6-SUBSTITUTED PURINYL PIPERAZINE DERIVATIVES

[75] Inventors: Zoltan G. Hajos, Princeton; Ramesh M. Kanojia, Somerville; Jeffery B. Press, Rocky Hill, all of N.J.

[73] Assignee: Ortho Pharmaceutical Corporation, Raritan, N.J.

[*] Notice: The portion of the term of this patent subsequent to Oct. 24, 2006 has been disclaimed.

[21] Appl. No.: 337,984

[22] Filed: Apr. 14, 1989

Related U.S. Application Data

[63] Continuation-in-part of Ser. No. 163,487, Mar. 3, 1988, Pat. No. 4,876,257.

[51] Int. Cl.$^5$ ............... C07D 473/36; C07D 473/34; C07D 473/24
[52] U.S. Cl. .................................. 544/276; 544/265; 544/272; 544/277
[58] Field of Search ............... 544/265, 272, 276, 277; 514/253, 265, 266

[56] References Cited

U.S. PATENT DOCUMENTS

| | | | |
|---|---|---|---|
| 3,135,754 | 6/1964 | Hitchings et al. | 544/276 |
| 3,232,937 | 2/1966 | Hitchings et al. | 544/276 X |
| 3,238,207 | 3/1966 | Hitchings et al. | 544/276 X |
| 3,642,798 | 2/1972 | Nitta et al. | 544/272 X |
| 3,734,911 | 5/1973 | Bestian | 544/272 X |
| 3,919,226 | 11/1975 | Thiel et al. | 544/277 |
| 4,189,579 | 2/1980 | Dunbar et al. | 544/276 |
| 4,543,254 | 9/1985 | Kaneko et al. | 544/272 X |
| 4,564,617 | 1/1986 | Sugimoto et al. | 544/272 X |
| 4,678,789 | 7/1987 | Richardson et al. | 514/262 |
| 4,710,572 | 12/1987 | Abou Gharbia et al. | 544/267 |
| 4,849,423 | 7/1989 | Ott | 514/253 |
| 4,876,257 | 10/1989 | Hajos et al. | 514/253 |

FOREIGN PATENT DOCUMENTS

| | | | |
|---|---|---|---|
| 0095188 | 8/1981 | Japan | 544/272 |
| 1199065 | 7/1970 | United Kingdom | 544/272 |

*Primary Examiner*—Diana Rivers
*Attorney, Agent, or Firm*—Benjamin F. Lambert

[57] ABSTRACT

6-Substituted purinyl piperazine derivatives and a method of synthesis for the derivatives are described. The 6-substituted purinyl piperazine derivatives are useful as cardiotonic agents and antiarrhythmic agents.

4 Claims, No Drawings

6-SUBSTITUTED PURINYL PIPERAZINE DERIVATIVES

This is a continuation-in-part of application Ser. No. 163,487, filed Mar. 3, 1988 now U.S. Pat. No. 4,876,257.

BACKGROUND OF THE INVENTION

1. Field of the Invention

The present application relates to compounds of the formula:

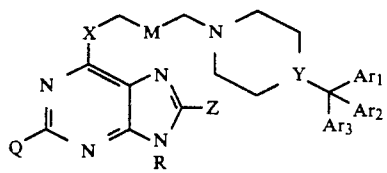

as further defined herein. The compounds are useful as cardiovascular agents. They possess positive ionotropic activity and are especially useful as cardiotonic agents for improving cardiac ejection, particularly in the setting of acute or chronic heart failure. The compounds are also useful as antiarrhythmic agents for the treatment or prevention of cardiac arrythmias.

2. Description of the Prior Art

British Patent Application No. GB2186573 and German Patent application No. DE3703633 relate to purine derivatives possessing cardiotonic and antiarrhythmic activity and having the following formula:

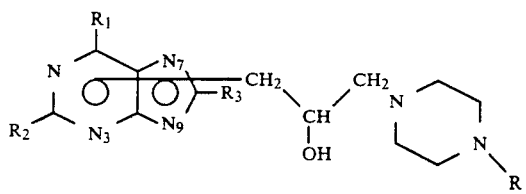

wherein R is an optionally substituted diphenylalkyl group. The side chain in the above formula is bonded to a ring nitrogen atom.

U.S. Pat. No. 4,460,586 relates to 3-aminopropoxyaryl derivatives of the formula:

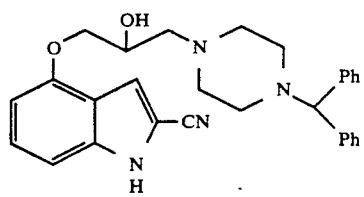

The compounds are useful as cardiotonic, antiarrhythmic and $\alpha$- and $\beta$-adrenoceptor blocking agents. The U.S. Patent is one of a series of patents that have issued claiming various 4-substituted indole derivatives.

SUMMARY OF THE INVENTION

The present invention is directed to 6-substituted purinyl piperazine derivatives of the general formula:

wherein

X is S, O, NH and $NR_1$ wherein $R_1$ is $C_1$-$C_4$-lower alkyl;

M is $CH_2$, CHOH, $CHOCOR_2$ and $CHOR_2$ wherein $R_2$ is straight or branched chain $C_1$-$C_8$- lower alkyl, phenyl and substituted Phenyl wherein the substituent on the phenyl ring is $C_1$-$C_4$- lower alkyl, $CF_3$, halo such as fluoro, chloro, bromo and iodo, $C_1$-$C_4$- lower alkyl, $C_1$-$C_4$- lower alkoxy, $NO_2$ and CN;

Y is $N(CH_2)_n$—wherein n is an integer from 0–4 or a carbon atom having a double bond (C=), both groups being attached to the carbon atom to which $Ar_1$, $Ar_2$ and $Ar_3$ are attached;

$Ar_1$, $Ar_2$ and $Ar_3$ are independently selected from H, $C_1$-$C_4$-lower alkyl, phenyl, substituted phenyl wherein the substituent is $C_1$-$C_4$-lower alkyl, $C_1$-$C_4$- lower alkoxy, $CF_3$, halo and perhalo such as fluoro, chloro, bromo and iodo, $NO_2$, CN; naphthyl, pyridyl and thienyl; provided that when X is NH or $NR_1$ and Y is N, $Ar_1$, and $Ar_2$ are other than hydrogen;

Z is H, CN, $C_1$-$C_4$-lower alkyl, halo such as fluoro, chloro, bromo and iodo, OH, $CO_2R_3$ wherein $R_3$ is H or $C_1$-$C_4$ lower alkyl, phenyl and substituted phenyl wherein the substituent is $C_1$-$C_4$-lower alkyl, $NO_2$, halo such as chloro, bromo, iodo or fluoro, CN and $CF_3$;

R is H, $C_1$-$C_4$-lower alkyl, cyclopentyl, cyclohexyl, benzyl, $C_2$-$C_6$-lower alkenyl, $C_2$-$C_6$-lower alkynyl, tetrahydropyranyl and tetrahydrofuranyl;

Q is halo such as fluoro, bromo, chloro and iodo; amino, $C_1$-$C_4$-lower alkyl and OH.

Also included are the optically active isomers of the 6-substituted purinyl piperazine derivatives.

In the above general formula at least one of $Ar_1$ $Ar_2$ and $Ar_3$ is an aromatic group and when Y is a carbon atom attached to a double bond (C=) only $Ar_1$ and $Ar_2$ are attached to the carbon atom.

The compounds of the general formula are useful as cardiovascular agents, and in particular as cardiotonic agents, and are also useful as antiarrhythmic agents

DETAILED DESCRIPTION OF THE INVENTION

The invention in its broadest aspects relates to 6-substituted purinyl piperazine derivatives which exhibit positive ionotropic activity.

The compounds of the present invention wherein X is sulfur can be prepared as outlined in Scheme 1.

SCHEME 1

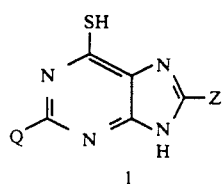

1

-continued
SCHEME 1

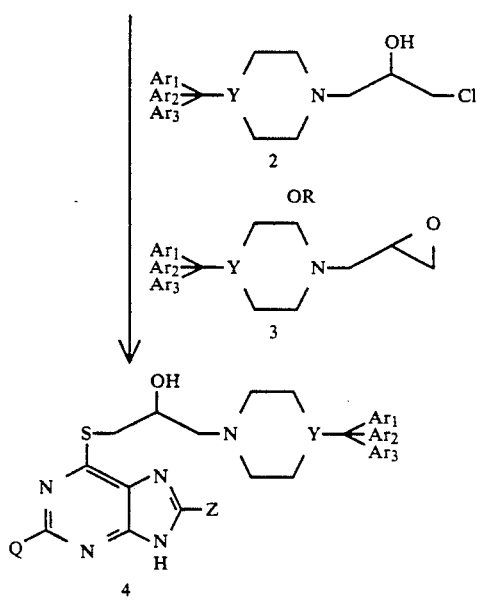

SCHEME 2

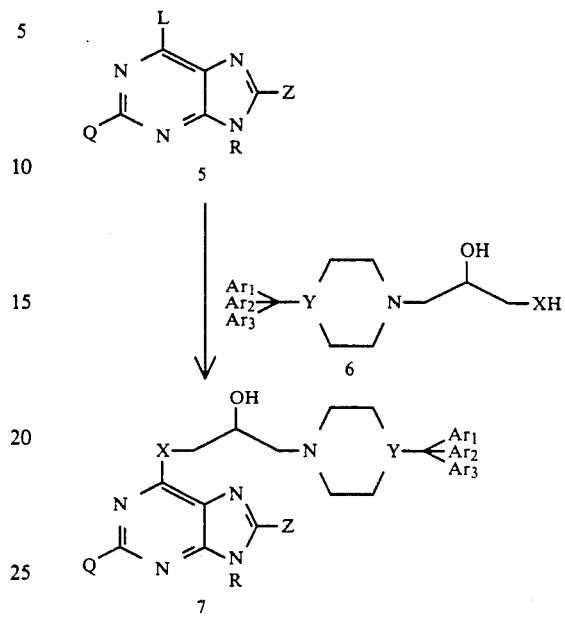

In this case, the appropriately substituted 6-mercaptopurine derivative 1 is treated with a base such as amines (for example, triethylamine), metal hydroxides (for example, sodium or potassium hydroxide), metal hydrides (for example, sodium hydride) in an inert solvent such as dimethylformamide (DMF) or tetrahydrofuran (THF). The anion so formed is reacted with appropriately substituted alkylating agents such as the chloride 2 or the epoxide 3 and the reactants are allowed to react for about 2 to 200 hours at a temperature of about 0° to 100° C. to form the compounds of the invention 4. The chlorides 2 and epoxides 3 used as the alkylating agents are either commercially available or they can be prepared by procedures found in the chemical literature and available to those skilled in the art.

Alternatively, the compounds of the present invention wherein X is sulfur (S), NH, $NR_1$ or oxygen (O) can be prepared by the procedure outlined in Scheme 2. An appropriately substituted purine 5 having a suitable leaving group (L) in the 6-position on the six membered ring is reacted with an appropriately substituted alcohol 6 where X is oxygen, with an amine where X is NH, $NR_1$, or with a mercaptan, where X is sulfur, in a suitable solvent such as benzene, toluene, DMF, DMSO or THF, for example. As the leaving group (L) a chloro, bromo or tosyl group may be employed. The purine starting material may or may not be Substituted at the N-9 position. The reaction may be carried out in the presence of a base and/or a catalyst. Suitable bases which can be employed include alkali metal and alkaline earth metal hydroxides and hydrides such as sodium or potassium hydroxide, and sodium or potassuim hydride, and sodium or potassuim metal. The reaction may also be carried out in the presence of a phase transfer or a crown ether catalyst such as 18-crown-6, for example. When the group at N-9 is a protecting group it can be removed by acid (in the case where R is tetrahydropyranyl or tetrahydrofuranyl) or hydrogenolysis (in the case where R is benzyl).

The compounds of the present invention can also be prepared as outlined in Scheme 3. An appropriately substituted alcohol 8 is reacted with an acid chloride, such as acetyl chloride or propionyl chloride, for example, or the corresponding acid anhydride in the presence of a base such as, for example, triethylamine or pyridine, in a suitable solvent such as THF or methylene chloride, for example, to form the ester derivative ($R_4$ is $COR_2$ wherein $R_2$ is as defined above). If an alkyl iodide such as methyl iodide, for example, is employed as the alkylating agent, the reaction is generally carried out in the presence of a strong base such as sodium hydroxide or sodium hydride, for example, to form the ether derivatives 10 ($R_4 = R_2$ wherein $R_2$ is as defined above). In those cases where R is tetrahydropyranyl, for example, the protecting group may be removed by hydrolysis with mild acid such as dilute hydrochloric acid.

The compounds of the present invention wherein X is sulfur can also be prepared as outlined in Scheme 4 where an appropriately substituted 6-mercaptopurine derivative 1 is treated with epichlorohydrin or glycidyl tosylate in either its racemic or optically active [(2R)-(−) or 2S-(+)] form in a suitable solvent, such as ethanol, acetonitrile, DMF or DMSO. The reaction is carried out at a temperature of about 0°–50° C. for a period of about several hours to about 10 days to give the chloride derivative 11. The reaction may optionally be carried out in the presence of a base such as sodium bicarbonate. Treatment of the chloride derivative 11 with an appropriately substituted benzhydryl piperazine 12 either neat or in the presence of a solvent at a temperature of about 15°–50° C. for from about several hours to several weeks results in the purinyl piperazine derivative 13 as racemic or optically active forms. Suitable solvents that can be employed in the reaction include methanol, ethanol, DMF and DMSO.

SCHEME 3

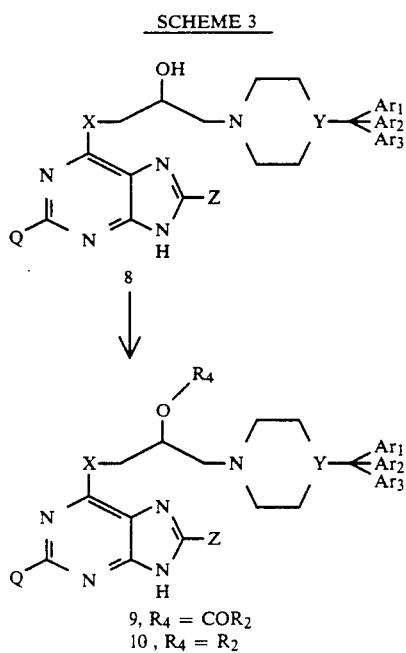

9, R₄ = COR₂
10, R₄ = R₂

SCHEME 4

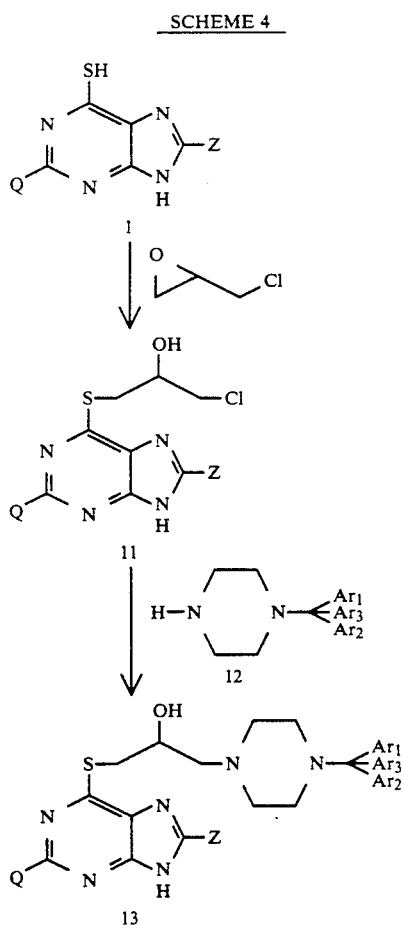

The benzhydryl piperazine compounds 12 are available commercially or they can be prepared according to literature Procedures known to those skilled in the art. Unsymmetrical triaryl compounds may be prepared by reacting an aromatic carboxylic acid derivative such as ethyl 2-naphthalenecarboxylate with an organometallic reagent such as 2-pyridyl lithium under controlled conditions to give 2-naphthyl 2pyridyl ketone. This in turn may be reacted with an organometallic reagent such as 2-thienyl lithium to give 1-(2-naphthyl)-1-(2-pyridyl)-1-(2-thienyl)methanol. This alcohol may in turn be reacted with halogenating agents such as thionyl chloride to give the corresponding chloromethane derivative in a manner similar to that described in Procedure 12. Reaction with piperazine in a like manner as described in Procedure 12 gives the requisite piperazine derivative. By varying the aromatic carboxylic acid derivative and the choice of the organometallic reagents in this procedure, a variety of tris- and bis-unsymmetrical benzhydryl piperazine derivatives may be prepared.

Those compounds wherein Z is other than hydrogen can be prepared as follows: Using procedures described by M. Ishidate and H. Yuki [Chem. Pharm. Bull., 5,240 (1957)], 8-carboxyhypoxanthine can be prepared. Esterification using standard conditions gives 8-carbomethoxyhypoxanthine. Reaction of this ester with concentrated ammonia gives 8-carboxamidohypoxanthine which may be dehydrated using standard conditions to give 8-cyanohypoxanthine. These hypoxanthine derivatives may be converted using phosphorus pentasulfide by the procedure of F. Bergmann and M. Tamari (J. Chem. Soc., 4468 (1961)) to the corresponding 6-mercaptopurine derivatives. Alternatively, they may be converted to the corresponding 6-chloropurine derivatives by the action of phosphorus pentachloride using standard reaction conditions. 8-Methyl of other 8-alkyl purine derivatives may be prepared using procedures as outlined by F. Bergman et al., J. Chem. Soc. (C). 1254 (1967). 6-Mercaptopurine substituted at the 2-position such as 2-chloro-6-mercaptopurine or 2-hydroxy-6-mercaptopurine may be obtained as described by R. K. Robins (J. Amer. Chem. Soc., 80, 6671 (1958)).

The 6-mercaptopurine derivatives may be reacted with appropriate piperazinyl chlorohydrin derivatives according to the procedure described in Examples 1, 23 and 24 to give the compounds of this invention wherein X=S. The 6-chloropurine derivatives may be reacted with piperazinyl hydroxypropylamines as described in Examples 21 and 32 to give the compounds of this invention wherein X=NH or X=NR₁ or with piperazinyl propane-1,2-diols as in Example 18 to give the compounds of this invention wherein X=O.

Preparation of the compounds of this invention wherein Y is $N(CH_2)_n$—where n is other than 0 is accomplished by preparing the appropriate N-arylalkylpiperazines according to procedures described by G. L. Regnier et al. (J. Med. Chem., 15, 295 (1972)) or by Neth. Appl. 6,507,312 (Chem. Abstr., 64, 12704 g (1964) assigned to Janssen Pharmaceutica. These piperazines may then be reacted with epichlorohydrin in a manner analogous to part (a) of example 23 and the resultant product converted to one of the compounds of this invention using the technique as outlined in part (b) of Example 23.

Pharmaceutical compositions containing a compound of the present invention as the active ingredient in intimate admixture with a pharmaceutical carrier can be prepared according to conventional pharmaceutical compounding techniques. The carrier may take a wide variety of forms depending on the form of preparation desired for administration, e.g., intravenous, oral or parenteral. The composition may also be administered by means of an aerosol. In preparing the compositions in oral dosage form, any of the usual pharmaceutical media may be employed, such as, for example, water, glycols, oils, alcohols, flavoring agents, preservatives, coloring agents and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. If desired, tablets may be sugar-coated or enteric-coated by standard techniques. For parenterals, the carrier will usually comprise sterile water, though other ingredients, for example, to aid solubility or for preservative purposes, may be included; injectable suspensions may also be prepared, in which case appropriate liquid carriers, suspending agents and the like may be employed. The pharmaceutical compositions will generally contain a dosage unit, e.g., tablet, capsule, powder, injection, teaspoonful and the like, from about 0.01 to about 50 mg/kg, and preferably from about 0.1 to about 10 mg/kg of the active ingredient.

The following examples describe the invention in greater particularity and are intended to be a way of illustrating but not limiting the invention. Some of the compounds in the examples were obtained as the hydrate. The water can be removed from the hydrates by drying at temperatures below the melting point of the compound.

EXAMPLE 1

6-[1-[1-[Bis(4-fluorophenyl)methyl]piperazin-4-yl]-2-hydroxy-3-propanylthio] purine Hemihydrate To DMF (7 mL), 6-mercaptopurine (5 mmol, 0.85 g) was added in portions and the solution was stirred at room temperature, under $N_2$ for 5 min. $Et_3N$ (5 mmol, 0.69 mL) was added dropwise. After 5 min, 1-(1-chloro-2-hydroxy-3-propanyl)-4-[bis(4-fluorophenyl)- methyl]-piperazine (5 mmol, 1.9 g) in DMF (5 mL) was added dropwise over 5 min at room temperature under $N_2$. After 22 h, the solution was filtered through a sintered glass funnel and the filtrate was evaporated (1.0 mm Hg, 50° C., stirring). Silica gel flash chromatography of the crude product (2.34 g) using 10% $MeOH:CH_2Cl_2$ gave pure product, 0.630 g (25.4%), mp 115°–116° C. (dec). DCI/MS (M+1) 497. 400 MHz $^1H$ NMR ($CDCl_3$) δ: 8.6 (s, 1H), 8.25 (s, 1H), 7.35 (m, 4H), 6.95 (m, 4H), 4.2 (s, 1H), 4.15 (m, 1H), 3.45 and 3.6 (m, 2H), 2.65 (m, 2H), 2.6 (m, 4H), 2.4 (m, 4H).

Anal. Calcd. for $C_{25}H_{26}F_2N_6OS.\frac{1}{2} H_2O$: C, 59.40; H, 5.38; N, 16.62.

Found: C, 58.88; H, 5.34; N, 16.56.

EXAMPLE 2

(2S)-(+)-6-[1-[1-[Bis(4-fluorophenyl)methyl]piperazin-4-yl]-2-hydroxy-3-propanylthio]purine To NaH (0.56 g, 11.6 mmol, 50% suspension in mineral oil prewashed with pentane) in DMF (12 mL) at 0° C. 6-mercaptopurine (1.97 g, 11.6 mmol) was added in portions over 10 min. (2S)-(−)-(1,2-Epoxypropyl)-4-[bis(4-fluorophenyl)methyl]piperazine (4.0 g, 11.6 mmol) in DMF (10 mL) was added dropwise at 0° C. over a 5 min period. The reaction mixture was allowed to warm to room temperature after an additional 5 min and was stirred for 72 h. DMF was removed in vacuo (1 mm Hg, 55° C.) and the residue was dissolved in $CH_2Cl_2$ (100 mL). The solution was filtered through celite, concentrated and the residue was purified by flash chromatography on silica gel using 10% $MeOH:CH_2Cl_2$ to give the title compound as a white solid, 1.37 g (23%), mp 118°–120° C. (dec.); DCI/MS (M+1) 497. 400 MHz $^1H$ NMR ($CDCl_3$) δ: 8.65 (s, 1H), 8.2 (s, 1H), 7.35 (m, 4H), 6.98 (m, 4H), 4.2 (s, 1H), 4.18 (m, 1H), 3.65–3.45 (m, 2H), 2.7–2.4 (m, 10H); $[δ]_D^{22}$ +7.3° (0.5% in EtOH).

Anal. Calcd. for $C_{25}H_{26}F_2N_6OS$: C, 60.46; H, 5.28; N, 16.92. Found: C, 60.12; H, 5.43; N, 16.94.

EXAMPLE 3

(2R)-(−)-6-[1-[1-[Bis(4-fluorophenyl)methyl]piperazin-4-yl]-2-hydroxy-3-propanylthio]purine In a manner similar to Example 2, when (2R)-(+)-(1,2-epoxypropyl)-4-[bis(4-fluorophenyl)methyl]piperazine (2.18 g, 6.33 mmol) was used, the title compound was isolated as a white crystalline solid, 0.61 g (20%), mP 118°–120° C. (dec.); DCI/MS (M+1) 497. 400 MHz $^1H$ NMR ($CDCl_3$) δ: 8.63 (s, 1H), 8.20 (s, 1H), 7.32 (m, 4H), 6.95 (m, 4H), 4.20 (s, 1H), 4.15 (m, 1H), 3.55 (m, 2H), 2.7–2.4 (m, 10H); $[δ]_D^{22}$ −7.3° (0.5% in EtOH).

Anal. Calcd. for $C_{25}H_{26}F_2N_6OS$: C, 60.46; H, 5.28; N, 16.92. Found: C, 60.31; H, 5.71; N, 16.53.

EXAMPLE 4

6-[2-Hydroxy-3-(1-(diphenylmethyl)piperazin-4-yl)propan-1-yl]triopurine Hemihydrate To DMF (6 mL), sodium hydroxide pellets (200 mg, 5 mmol) and 6-mercaptopurine monohydrate (0.85 g, 5 mmol) were added. The reaction mixture was stirred and heated to 80° C. for 30 min under nitrogen. The almost clear solution was cooled to room temperature and 1-(1-chloro-2-hydroxy-3-propanyl)-4-(diphenylmethyl)piperazine (1.72 g, 5 mmol) in DMF (10 mL) was added within 5 min. After stirring under nitrogen for 72 h, the mixture was filtered through Celite on a sintered glass funnel and the funnel was rinsed with DMF (2×5 mL). Evaporation of the solvent from the filtrate at 1.0 mm Hg at 50° C. gave a residue which was triturated with 10% methanol/methylene chloride. Filtration removed unreacted 6-mercaptopurine (0.5 g). The solution was purified using flash chromatography on silica gel using 10% methanol/methylene chloride as eluant. The product was isolated by concentration of the desired fractions and purified by trituration with n-pentane to give the title compound (0.35 g, 15.0%), mp 105°–110° C. (dec). DCI/MS M+1 461. 100 MHz $^1H$ NMR (DMSO-$d_6$) δ: 8.6 (s, 1H), 8.18 (s, 1H), 7.2–7.4 (m, 10H), 4.21 (s, 1H) 4.20 (m, 1H), 3.5 (m, 2H), 2.6 (m, 2H), 2.5–2.6 (m, 8H).

Anal. Calcd. for $C_{25}H_{28}N_6OS.\frac{1}{2} H_2O$: C, 63.94; H, 6.22; N, 17.90. Found: C, 64.04; H, 6.51; N, 17.86.

EXAMPLE 5

6-[1-[1-(Benzyl)piperazin-4-yl]-2-hydroxy-3-propanylthio]purine Monomalonate.5/2 Hydrate 6-Mercaptopurine (0.85 g, 5 mmol) and $Et_3N$ (0.7 mL, 5 mmol) were added to DMF (7 mL). After 10 min, 1-(1-chloro-2-hydroxy-3-propanyl)-4-benzylpiperazine (1.27 g, 5 mmol) in DMF (10 mL) was added dropwise over 5 min under nitrogen. After 96 h the DMF was removed in vacuo to give the crude product (1.99 g). Flash chromatography using silica gel and 10% MeOH:CH$_2$Cl$_2$ gave pure base (1.01 g, 52.6%). To this white solid (700 mg, 1.82 mmol) dissolved in MeOH (5 mL) malonic acid (0.96 M, 1.82 mmol, 1.9 mL) was added dropwise over 5 min under nitrogen. After 5 h, the MeOH was removed in vacuo and the resultant solid was dried further under vacuum at 40° C. to give the pure title compound (0.860 g, 92.76%, overall yield 48.8%), mp 175° C. (dec.) DCI/MS (M+1) 385. 400 MHz $^1$H NMR (DMSO-d$_6$) δ: 8.7 (s, 1H), 8.4 (s, 1H), 7.35 (M, 5H), 4.1 (m, 1H), 3.7 (s, 2H), 3.4–3.6 (m, 2H), 2.95 (s, 2H), 2.5–2.9 (m, 10H).

Anal. Calcd. for C$_{19}$H$_{24}$N$_6$OS.C$_3$H$_4$O$_4$.5/2H$_2$O: C, 49.52; H, 6.23; N, 15.75. Found: C, 49.58; H, 5.95; N, 15.55.

EXAMPLE 6

6-[3-[4-(1,3-Benzodioxol-5-yl)methyl]piperazin-1-yl]-2-hydroxyprop-1-ylthio] purine Sesquihydrate 6-Mercaptopurine (0.850 g, 5 mmol) and Et$_3$N (0.7 mL, 5 mmol) were added to DMF (7 mL). After 10 min, 1-(1-chloro-2-hydroxy-3-propanyl)-4-piperonylpiperazine (1.56 g, 5 mmol) in DMF (10 mL) was added dropwise over 5 min under nitrogen. After 96 h and removal of the precipitated NaCl by filtration, the DMF was removed in vacuo to give the crude product (1.99 g). Flash chromatography using silica gel and 10% MeOH:CH$_2$Cl$_2$ gave the pure product (1.01 g, 47.2%) as a white solid, mp 138°–140° C. DCI/MS (M+1) 429. 400 MHz $^1$H NMR (DMSO-d$_6$) δ: 8.65 (s, 1H), 8.45 (s, 1H), 6.85 & 6.75 (m, 3H), 6.0 (s, 2H), 3.95 (m, 1H), 3.70 (m, 2H), 3.35 (s, 1H), 3.30 (m, 2H), 2.3–2.6 (m, 8H).

Anal. Calcd. for C$_{20}$H$_{24}$N$_6$O$_3$S.3/4H$_2$O: C, 52.74; H, 5.97; N, 18.45. Found: C, 52.98; H, 5.56; N, 18.40.

EXAMPLE 7

6-[1-[1-(4-Chlorobenzhydryl)]piperazin-4-yl]-2-hydroxy-3-propanylthio]purine Monohydrate 6-Mercaptopurine (0.850 g, 5 mmol) and Et$_3$N (0.7 mL, 5 mmol) were added to DMF (7 mL). After 10 min, 1-(1-chloro-2-hydroxy-3-propanyl)-4-(4-chlorobenzhydryl)piperazine (1.9 g, 5 mmol) in DMF (10 mL) was added dropwise over 5 min at room temperature under nitrogen. After 7 days, the resultant solution was filtered and the DMF removed in vacuo giving the crude product (2.5 g). Silica gel flash chromatography using 10% MeOH:CH$_2$Cl$_2$ gave the desired product (1.0 g, 40.5%) as a white solid; mp 117°–120° C. (dec). DCI/MS (M+1) 495. 400 MHz $^1$H NMR (CDCl$_3$) δ: 8.6 (s, 1H), 8.2 (s, 1H), 7.35 (m, 4H), 7.2 (m, 4H), 4.25 (m, 1H), 4.2 (s, 1H), 3.4–3.6 (m, 2H), 2.8 (m, 6H), 2.4 (m, 4H).

Anal. Calcd. for C$_{25}$H$_{27}$ClN$_6$OS.H$_2$O: C, 58.55; H, 5.70; N, 16.39. Found: C, 58.86; H, 5.53; N, 16.35.

EXAMPLE 8

6-[1-[1-(Triphenylmethyl)piperazin-4-yl]-2-hydroxy-3-propanylthio]purine Monohydrate 1-(1-Chloro-2-hydroxy-3-propoxy)-4-(triphenylmethyl) piperazine (2.3 g, 5.5 mmol) was reacted as above with with 6-mercaptopurine to give the title compound as an off-white solid, 0.63 g (21.3%), mp 158–161° C. DCI/MS (M+1) 537. 400 MHz $^1$H NMR (CDCl$_3$) δ: 8.55 (s, 1H), 8.15 (s, 1H), 7.45 (m, 4H), 7.25 (m, 4H), 4.15 (m, 1H), 4.15 (m, 1H), 3.59 (dd, 1H, J=4.85 Hz), 3.45 (dd, 1H, J=7.27 Hz). 2.8–2.4 (m 10H).

Anal. Calcd. for C$_{31}$H$_{32}$N$_6$OS.H$_2$O: C, 67.12; H, 6.18; N, 15.15. Found: C, 67.29; H, 5.91; N, 14.96.

EXAMPLE 9

6-[1-[1-(Carboethoxy)piperazin-4-yl]-2-hydroxy-3-propanylthio]purine 1-(1-Chloro-2-hydroxy-3-propoxy)-4-carboethoxypiperazine (1.24 g, 5.0 mmol) was reacted as above with 6-mercaptopurine to give the title compound as a clear oil, 120 mg (6.54%). DCI/MS (M+1) 367. 400 MHz $^1$H NMR (CDCl$_3$) δ: 8.7 (s, 1H), 8.2 (s, 1H), 4.15 (q, 2H, J=4.85 Hz), 3.6 (m, 2H), 3.5 (m 4H), 2.6 (m, 4H), 2.45 (m, 2H), 2.25 (t, 3H, J=4.85 Hz).

Anal. Calcd. for C$_{15}$H$_{22}$N$_6$O$_3$S: C, 49.17; H, 6.05; N, 22.93. Found: C, 49.35; H, 6.24; N, 22.09.

EXAMPLE 10

6-[1[1-(3,4'[Bis(trifluoromethylphenyl)methyl])piperazin-4-yl]-2-hydroxy-3-propanylthio]purine 1-(1-Chloro-2-hydroxy-3-propoxy)-4-[bis(3,4'-trifluoromethylphenyl)methyl]piperazine (1.0 g, 2.1 mmol) was reacted as above with 6-mercaptopurine to give the title compound as an off-white solid, 160 mg g (12.8%), mp 108°–110° C. DCI/MS (M+1) 597. 400 MHz $^1$H NMR (CDCl$_3$) δ: 8.65 (s, 1H), 8.3 (s, 1H), 7.65 (s, 1H), 7.59–7.4 (m, 7H), 4.39 (s, 1H), 4.15 (m, 1H), 3.65 (dd, 1H, J=4.86 Hz), 3.5 (dd, 1H, J=7.29 Hz), 2.7–2.4 (m, 10H).

Anal. Calcd. for C$_{27}$H$_{26}$F$_6$N$_6$OS: C, 54.37; H, 4.39; N, 13.99. Found C, 54.42; H, 4.21; N, 14.09.

EXAMPLE 11

6-[1-[1-[Bis(4-fluorophenyl)methyl]piperazin-4-yl]-2-acetoxy-3-propanylthio]purine ¾Hydrate To a solution of 6-[1-[1-[bis(4-fluorophenyl)methyl]-piperazin-4-yl]-2-hydroxy-3-propanylthio]purine (1.0 g, 0.002 mol) in CH$_2$Cl$_2$ (7 mL), acetic anhydride (0.2 mL, 0.002 mol) in Et$_3$N (0.2 mL, 0.002 mol) was added dropwise over 5 min at room temperature under nitrogen. After 70h, CH$_2$Cl$_2$ (50 mL) was added and the solution was extracted with saturated NaHCO$_3$ (2×100 mL), H$_2$O (1×100 mL), and saturated brine (1×100 mL); the organic layer was dried over Na$_2$SO$_4$. Solvent removal of the dried organic layer gave a solid which was dried in vacuo at 40° C. to give pure product (0.7 g, 64.8%), mp 105°–109° C. (dec). DCI/MS (M+1) 539. 400 MHz $^1$H NMR (CDCl$_3$) δ: 8.7 (s, 1H), 8.2 (s, 1H), 7.3 (m, 4H), 6.95 (m, 4H), 5.3 (m, 1H), 4.2 (s, 1H), 3.4 and 4.0 (m, 2H), 2.65 (m, 2H), 2.6 (m, 4H), 2.4 (m, 4H), 2.0 (s, 3H).

Anal. Calcd. for C$_{27}$H$_{28}$F$_2$N$_6$O$_2$S.¾ H$_2$O: C, 58.74; H, 5.38; N, 15.22. Found: C, 58.69; H, 5.37; N, 15.02.

EXAMPLE 12

6-[1-[1-[Bis(4-fluorophenyl)methyl]piperazin-4-yl]-2-(2,2,2-trimethylacetoxy)propanylthio]purine To 6-[1-[1-[bis(4-fluorophenyl)methyl]-piperazin-4-yl]-2-hydroxy-3-propanylthio]-purine (4.04 g, 8 mmol) in CH$_2$Cl$_2$ (5 mL), trimethylacetic anhydride (8 mmol, 1.62 mL) in Et$_3$N (1.15 mL, 8 mmol) was added dropwise under nitrogen. After 21 h an additional equivalent of the anhydride was added. After 92 h and silica gel flash chromatography (10% MeOH:CH of the solvent free residue, crude Product was obtained. The crude product was dissolved in CH (10 mL) and stirred with saturated NaHCO$_3$ (10 mL) for 16 h. The CH$_2$Cl$_2$ was separated and extracted with H$_2$O (1×) and saturated NaCl (1×), dried over Na$_2$SO$_4$ and the CH$_2$Cl$_2$ removed in vacuo to give pure product (0.88 g, 37.5%) as a white solid. mp 102°–104° C. (dec.). DCI/MS (M+1) 581. 400 MHz $^1$H NMR (CDCl$_3$) δ: 8.7 (s, 1H), 8.2 (s, 1H), 6.95 (m, 4H), 7.35 (m, 4H), 5.4 (m, 1H), 4.2 (s, 1H), 3.5 & 4.0 (m, 2H), 2.65 (m, 2H), 2.4 & 2.6 (m, 8H), 1.15 (S, 9H).

Anal. Calcd. for C$_{30}$H$_{34}$F$_2$N$_6$O$_2$S: C, 62.05; H, 5.90; N, 14.47. Found: C, 61.85; H, 5.98; N, 14.04.

EXAMPLE 13

6-[1-[1-[Bis(4-fluorophenyl)methyl]piperazin-4-yl]-2-(3,4,5-trimethoxybenzoyloxy)- 3-propanylthio]purine Trimethoxybenzylchloride (0.92 g, 4 mmol) in Et$_3$N (0.4 mL, 4 mmol) and CH$_2$Cl$_2$ (2 mL) were added dropwise at 0° C. to 6-[1-[1-[bis(4-fluorophenyl)methyl]piperazin-4-yl]-hydroxy-3-propanylthio]purine (2 g, 4 mmol) in CH$_2$Cl$_2$ (3 mL). After 16 h the solution was filtered and the filtrate concentrated in vacuo followed by silica gel flash chromatography (10% MeOH:CH$_2$Cl$_2$) to give crude product 20 −2.23 g). The crude product was dissolved in ether (50 mL) and pentane (10 mL) and the resultant precipitate isolated as a white solid, (0.83 g, 30.0%), mp 114°–118° C. (dec). DCI/MS (M+1) 691. 400 MHz $^1$H NMR (CDCl$_{13}$) δ: 8.55 (s, 1H), 8.15 (s, 1H), 6.95–7.3 (m, 8H), 7.2 (s, 2H), 5.78 (m, 1H), 4.2 (s, 1H), 3.9 (s, 1H), 3.8 (s, 2H), 3.4 (m, 2H), 2.8 (m, 2H), 2.5–2.4 (m, 8H).

Anal. Calcd. for C$_{35}$H$_{36}$F$_2$N$_6$O$_5$S: C, 60.86; H, 5.25; N, 12.17. Found: C, 60.65; H, 5.32; N, 12.01.

EXAMPLE 14

6-[1-[1-Bis(4-fluorophenyl)methyl]piperazin-4-yl]-3-propanylthio]purine

Pentane (10 mL) was added to sodium hydride (0.3 g, 6.3 mmol, 50% suspension in mineral oil), and the mixture was stirred under nitrogen. The pentane was decanted, anhydrous DMF (12 mL) was added and the suspension was cooled to 0° C. 6-Mercaptopurine monohydrate (0.93 g, 5.5 mmol) was added in small portions over a 15 min period. To the light beige, slightly hazy mixture was added, after an additional 10 min at 0° C., 1-(1-chloro-3-propanyl)-4-[bis(4-fluorophenyl)methyl]-piperazine (2.0 g, 5.5 mmol) dissolved in anhydrous DMF (4 mL) within 5 min. After addition was complete, the mixture was allowed to warm to room temperature and it was stirred under nitrogen for 4 days. The DMF was evaporated in vacuo (1 mm Hg) at 50° C. The residue was triturated in methylene chloride and the mixture was filtered through celite. The filtrate was washed with water (2×50 mL), dried (sodium sulfate), filtered, and evaporated in vacuo to give the crude product (2.79 g). Silica gel flash chromatography using 10% methanol/methylene chloride gave the desired product (1.18 g, 45%) mp 90°–93° C. 300 MHz $^1$H NMR (CDCl$_3$) δ: 8.60 (s, 1H), 8.14 (s, 1H), 7.31 (m, 4H), 6.95 (m, 4H), 4.17 (s, 1H), 3.38 (m, 2H), 2.35–2.6 (m, 10H), 2.02 (m, 2H). DCI/MS (M+1) 481.

Anal. Calcd. for C$_{25}$H$_{26}$F$_2$N$_6$S: C, 62.61; H, 5.25; N, 17.53. Found: C, 62.38; H, 5.46; N, 17.62.

EXAMPLE 15

6-[1-[4-[Bis(4'-fluorophenyl)methylene]-1-piperidinyl]-2-hydroxy-3-propanylthio]- purine Hemihydrate To benzyl 4-[bis(4-fluorophenyl)methylene]-1-piperidine (8.0 g, 21 mmol) dissolved in MeOH (140 mL), 10% Pd/C (4.0 g) dispersed in MeOH was added under nitrogen, followed by the addition of ammonium formate (6.3 g, 100 mmol). The reaction mixture was stirred and refluxed. The resultant solution was filtered over celite under nitrogen. Evaporation in vacuo gave an oil which solidified upon standing overnight to give the debenzylated piperidine derivative (5.99 g, 100%).

To the piperidine derivative isolated above (6.0 g, 21 mmol) dissolved in EtOH (60 mL) with NaHCO$_3$ (1.8 g, 21 mmol) epichlorohydrin (1.7 mL, 22 mmol) in EtOH (20 mL) was added dropwise at 0° C. under nitrogen. After 30 min the reaction mixture was allowed to come to room temperature. After 24 h, removal of the EtOH in vacuo gave the crude product (7.86 g). Silica gel flash chromatography using 10% MeOH:CH$_2$Cl$_2$ gave the pure chloropropyl derivative (4.0 g, 50%).

To NaH (280 mg, 5.8 mmol, 50% suspension in mineral oil, pentane washed and removed) in DMF (12 mL) at 0° C. was added 6-mercaptopurine (850 mg, 5 mmol) was added in portions over 15 min, under nitrogen. After 1 h, the chloride obtained above (2.08, 5 mmol) in DMF (14 mL) was added over 15 min at 0° C., under nitrogen. The reaction mixture was allowed to warm to room temperature for 3 days and then was heated to 70° C. under nitrogen for 1 day. Solvent removal in vacuo and extraction of the residue with CH$_2$Cl$_2$ gave crude product (2.4 g). Silica gel flash chromatography using 10% MeOH:CH$_2$Cl$_2$ gave the title compound (1.28 g). Further trituration of this product with pentane (100 mL) gave pure product (0.73 g, 29.2%), mp 107°–110° (dec). DCI/MS (M+1) 494. 400 MHz $^1$H NMR (CDCl$_3$) δ: 8.65 (s, 1H), 8.25 (s, 1H), 7.16 (m, 4H), 6.9 (m, 4H), 4.2 (m, 1H), 3.55–3.65 (m, 2H), 2.4–2.7 (m, 2H).

Anal. Calcd. for C$_{26}$H$_{25}$F$_2$N$_5$OS.½H$_2$O: C, 62.13; H, 5.21; N, 13.94. Found: C, 62.24; H, 4.80; N, 14.38.

EXAMPLE 16

6-[1-[1-[Bis(4-chlorophenyl)methyl]piperazin-4-yl]-2-hydroxy-3-propanylthio]purine. 5/4 Hydrate Et$_3$N (0.7 mL, 5 mmol) was added to 6-mercaptopurine (0.85 g, 5 mmol) in DMF (7 mL). After 5 min 1-(1-chloro-2-hydroxy-3-propanyl)-4-[bis(4-chlorophenyl)-methylpiperazine (2.07 g, 5 mmol) in DMF (13 mL) was added dropwise over 5 min, under nitrogen. After 14 days and filtration of the resultant NaCl the DMF was removed in vacuo to give the crude product. Silica gel flash chromatography using 10% MeOH:CH$_2$Cl$_2$ gave the desired product (0.710 g) containing some DMF. The product was dissolved in CH$_2$Cl$_2$ (100 mL) and extracted with H$_2$O (2×25 mL) and saturated NaCl (1×25 mL), dried over Na$_2$SO$_4$, and the CH$_2$Cl$_2$ removed in vacuo to give pure product (0.590 g, 22.3%), mp 120°–124° C. (dec.) DCI/MS (M+1) 529 400 MHz $^1$H NMR (CDCl$_3$) δ: 8.6 (s, 1H), 8.2 (s, 1H), 7.25 (m, 8H), 4.2 (s, 1H), 4.1 (m, 1H), 3.6 (m, 2H), 2.7 (m, 2H), 2.3–2.6 (m, 8H).

Anal. Calcd. for C$_{25}$H$_{26}$Cl$_2$N$_6$OS.5/4H$_2$O: C, 54.39; H, 5.20; N, 15.22. Found: C, 54.03; H, 4.76; N, 14.91.

EXAMPLE 17

[3-[4-[bis(4-fluorophenyl)methyl]piperazin-1-yl]-2-hydroxypropoxy]-9-(tetrahydropyran-2-yl)purine To a stirred mixture of 6-chloro-9-(tetrahydro-2-pyranyl)purine (2.387 g, 10 mmol) in toluene (40 mL), powdered KOH (1.22 g, 21.4 mmol) and 18-crown-6 (0.132 g, 0.5 mmol) a solution of 3-[4-[di((4-fluorophenyl)methyl]-1-piperazinyl]-1,2-propanediol (3.8 g, 10.25 mmol) in toluene (80 mL) was added dropwise over a period of 5 min. After 3 h of stirring at room temperature the reaction mixture was treated with ice-cold water (70 mL). The organic layer was separated and washed with ice-water (4×70 mL), dried (Na$_2$SO$_4$), filtered and evaporate in vacuo to yield a foam (about 6 g) which was eluted through a silica gel column at medium pressure using increasing proportions of MeOH in CH$_2$Cl$_2$ as eluant. The fractions were pooled to give several major components. The faster moving fraction (I) was the bis-purinyl compound (1.14 g,). The middle fraction was the title compound (1.26 g, colorless foam) which softened at 115° C. and melted 120°-125° C. IR(KBr) cm$^{-1}$: 3400, 1602, 1578, 1506, 1341, 1224; $^1$H NMR (CDCl$_3$) δ: 8.52(s, 1H, 2 or 8-H), 8.14 (s, 1H, 2 or 8-H), 6.9-7.4 (m, 8H, Ar—H), 5.76 (d, 1H, N—CH—O—C), 4.63 (m, 2H, OCH$_2$), 4.21 [s,1H, CH(O—F)$_2$], 4.20 (m, 3.79 (m, 1.5-2.9 (m); MS 565 (MH)$^+$.

Anal. Calcd. for C$_{30}$H$_{34}$F$_2$N$_6$O$_3$.¼H$_2$O; C, 63.31; H, 6.11; N, 14.77. Found: C, 63.15; H, 5.85; N, 14.88.

EXAMPLE 18

6-[3-[4-Bis(4-fluorophenyl)methyl]piperazin-1-yl-2-hydroxy]propoxypurine

6-[3-[4-[Bis(4-fluorophenyl)methyl]piperazin-1-yl]-2-hydroxypropoxy]-9-(tetrahydro-2-pyranyl)purine (0.84 g, 1.488 mmol) was dissolved in glacial acetic acid (50 mL) and the resultant solution was diluted with water (30 mL). The aqueous solution was stirred at room temperature for 18 h, evaporated to dryness and the residue was treated with saturated aqueous sodium bicarbonate (100 mL). The precipitated solid was collected by filtration and washed with water and ether. The ether soluble portion of the solid was recovered starting material. The ether insoluble portion was re-extracted with boiling ether/CH$_2$Cl$_2$ (100 mL) and the insoluble solid isolated to give the purified title compound (380 mg, 53%), mp 147°-155° C. IR (KBr) cm$^{-1}$: 3327, 3365, 1605, 1506; $^1$H NMR (DMSO-d$_6$) δ: 8.45 (s, 1H, 2 or 8-H), 8.37 (br, 1H, 2 or 8-H), 7.05-7.50 (m, 8H, Ar-H), 4.54 (m, 1H, OCHH), 4.38 (m, 1H, OCHH); MS(DCI): 481 (MH)$^+$.

Anal. Calcd. for C$_{25}$H$_{26}$F$_2$N$_6$O$_2$: C, 62.49; H, 5.45; N, 17.49; F, 7.91. Found: C, 62.43; H, 5.27; N, 17.64; F, 7.76.

EXAMPLE 19

6-[3-[4-Diphenylmethyl)piperazin-1-yl]-2-hydroxypropoxyl]-9-(tetrahydro-2-pyranyl)-purine.¼ Hydrate To a solution of 6-chloro-9-(tetrahydro-2-Pyranyl)-purine (2.387 g, 1% mmol) in toluene (50 mL) were added potassium hydroxide (1.22 g, 21.4 mmol), 18-crown-6 (0.132 g, 0.05 mmol), and 2-[(4-phenylmethyl)-1-piperazinyl]-1,-2-propanediol (3.346 g, 10.25 mmol); the mixture was stirred vigorously for 2 h at room temperature and was heated to 90° C. for 14 h. After cooling, the reaction mixture was washed with water (4×100 mL); the organic layer was dried (Na$_2$SO$_4$), filtered and evaporated to dryness in vacuo to yield a foam (4.48 g). Purification on a silica gel column eluting with increasing proportions of MeOH in CH$_2$Cl$_2$ gave several fractions consisting of a mixture of several components; one set of fractions contained the title compound which was isolated as a foam, (0.63 g), mp: 90° C. (softening), 100°-110° C. melting. IR(KBr) cm$^{-1}$: 3420, 1601, 1317; $^1$H NMR (CDCl$_3$) δ: 8.58 (s, 1H, 2 or 8-H), 8.41 (s, 1H, 2 or 8-H), 7.1- 7.45 (m, 10H, Ar—H), 5.74 (m, 1H, N—CH—O—C), 4.58 (m, 2H, O—CH$_2$), 4.22 [s, 1H, CH(O)$_2$], 4.13 and 2.80 (br s each, 1H, OCH$_2$) 1.5-2.7 (br m, 16 H, N—CH$_2$ and OCH$_2$); MS: 529 (MH)$^+$.

Anal. Calc. for C$_{30}$H$_{36}$N$_6$O$_3$.¼H$_2$O: C, 67.50; H, 6.90; N, 15.76. Found: C, 67.25; H, 6.70; N, 15.99.

EXAMPLE 20

6-[3-[4-(Diphenylmethyl)piperazin-1-yl]-2-hydroxypropoxy]purine

6-[3-[4-Diphenylmethyl)piperazin-1-yl]-2-hydroxypropoxy]-9-(tetrahydro-2-pyranyl)purine (0.89 g, 1.68 mmol) was dissolved in glacial acetic acid (60 mL) and the resultant solution was diluted with water (40 mL). The aqueous solution was stirred at room temperature for 64 h and the reaction mixture was evaporated to dryness in vacuo. The residue was treated with 5% aqueous sodium bicarbonate (40 mL) and the precipitated solid was extracted with a mixture of ether:CH$_2$Cl$_2$ (3:1) (100 mL). The organic layer was filtered, washed with water, dried (Na$_2$SO$_4$) and evaporated to give the title compound as a colorless foam, 0.59 g (79%), mp. 115° C. (softening), 120°-130° C. (melting). IR (KBr) cm$^{-1}$: 3369, 3220, 1604, 1338, 1319, 113; $^1$H NMR (DMSO-d$_6$) δ: 8.45 (s, 1H, 2 or 8-H), 8.36 (s, 1H, 2- or 8-H), 7.1-7.5 (m, 10H, Ar-H), 4.56 (m, 1H, OCHH), 4.37 (m, 1H, OCHH), 4.23 [s, 1H, CH(O)$_2$]; MS: 446 (MH)$^+$.

Anal. Calcd. for C$_{25}$H$_{28}$N$_6$O$_2$: C, 67.55; H, 6.35; N, 18.91. Found: C, 67.34; H, 6.42; N, 18.99.

EXAMPLE 21

6-[3-4-[Bis(4-fluorophenyl)methyl]piperazin-1-yl]-2-hydroxypropylamino]purine

A mixture of 6-chloropurine (0.728 g, 4.7 mmol), 1-amino-3-[4-[bis(4-fluorophenyl)methyl]-1-piperazinyl]-2-propanol (1.73 g, 4.77 mmol) and triethylamine (1.36 mL, 9.5 mmol) in MeOH (20 mL) was heated to reflux for 7 days and the solvent was removed in vacuo. The residue was dissolved in CHCl$_3$ and the extracted with aqueous sodium bicarbonate (2×100 mL); the organic phase was dried over sodium sulfate and evaporated to give a solid which was purified by flash chromatography on silica gel with 5% MeOH in CHCl$_3$. The product was a colorless solid which was triturated with ether, 1.5 g (70%), mp 140-170° C.; IR (KBr) 3000 cm$^{-1}$; 300 MHz $^1$H NMR (CDCl$_3$); δ 8.17 (s, 1H), 8.11 (s, 1H), 7.5-7.0 (m, 8H), 4.90 (br s, 1H), 4.34 (s, 1H), 3.87 (br s, 1H), 3.7-2.0 (m, 12H); MS 480 (MH+).

Anal Calcd. for C$_{25}$H$_{27}$F$_2$N$_7$O: C, 62.62; H, 5.68; N, 20.45. Found: C, 62.55; H, 5.74; N, 20.10

EXAMPLE 22

6-[3-[4-[Bis(4-fluorophenyl)methyl]piperazin-1-yl]-2-acetoxypropylamino]purine.1.75 Hydrate Triethylamine (0.15 mL, 1.08 mmol) and acetic anhydride (0.08 mL, 0.85 mmol) were added to a solution of 4-[3-[4-[bis(4-fluorophenyl)methyl]piperazin-1-yl]-2-hydroxy propylamino]purine (350 mg, 0.730 mmol) in CH$_2$Cl$_2$ (5 mL) and the solution was stirred for 18 h. An additional amount of triethylamine (0.11 mL) and acetic anhydride (0.04 mL) was added and the mixture was stirred an additional 1 h. The mixture was extracted with aqueous sodium bicarbonate (2×20 mL), dried over sodium sulfate and concentrated to give a glass (0.45 g). Purification on silica gel with 2% MeOH in CHCl₃ gave the title compound as a colorless foam, 0.267 g (66%), mp 110–155° C.; IR (KBr) 1738 cm⁻¹; 300 MHz ¹H NMR (CDCl₃: δ 8.42 (s, 1H), 7.97 (s, 1H), 7.5–6.9 (m, 8H), 5.24 (br s, 1H), 4.23 (s, 1H), 3.87 (br s, 1H), 3.7–2.0 (m, 12H), 2.03 (s, 3H); MS 522 (MH⁺).

Anal Calcd. for $C_{25}H_{27}F_2N_7O.1\mu H_2O$: C, 58.63; H, 5.92; N, 17.72. Found: C, 58.75; H, 5.37; N, 17.66.

EXAMPLE 23

6-[1-[1-[Bis(3-trifluoromethylphenyl)methyl]piperazin-4-yl]-2-hydroxy-3-propanylthio]purine Hemihydrate a.

1-(1-Chloro-2-hydroxy-3-propanyl)-4-[(3,3′-trifluoromethyl)phenylmethyl] piperazine Hemihydrate

To epichlorohydrin (5 mmol, 4 mL) and NaHCO₃ (5 mmol, 0.420 9) in ethanol (5 mL) was added at 0° C. [(3,3′-trifluoromethyl)phenyl]piperazine (1.96 g, 5 mmol) in ethanol (25 mL) dropwise over 10 min under nitrogen. After 20 hours, the NaHCO₃ was removed by filtration and the ethanol removed in vacuo to give the crude product. Silica gel flash column chromatography using 5% MeOH:CH₂Cl₂ gave the desired product (2.16 g, 90.0%) as a clear oil. DCI/MS M+1 481; (400 MHz) ¹H NMR (CDCl₃) δ: 7.4–7.7 (m, 8H); 4.4 (s, 1H); 3.9 (m, 1H), 3.55 (m, 2H), 2.7 (m, 2H), 2.2–2.5 (m, 8H).

Anal Calcd. for $C_{22}H_{23}ClF_6N_6O.\frac{1}{2}H_2O$: C, 53.93; H, 4.73; N, 5.71. Found: C, 54.10; H, 4.71; N, 5.49.

b. Title compound

To a suspension of 6-mercaptopurine (3.5 mmol, 0.6 g) in DMF (7 mL) was added Et₃N (3.5 mmol, 0.5 mL) at room temperature. After stirring for 5 min, 1-(1-chloro-2-hydroxy-3-propanyl)-4-[bis(3-trifluoromethylphenyl)methylpiperazine](3.5 mmol, 1.7 g) in DMF (15 mL) was added dropwise over 5 min under nitrogen. After ten days, the DMF was removed in vacuo (1 mm Hg, 70° C.) to give the crude product. Silica gel flash column chromatography using 10% MeOH:CH₂Cl₂ gave pure product (1.0 g, 49.3%) as a white glassy solid; mp. 100°–105° C. (dec.), MS DCI (M+1) 597; (300 MHz) ¹H NMR (CDCl₃) δ: 8.6 (s,1H); 8.2 (s,1H); 7.4–7.7 (m,8H); 4.4 (s,1H); 4.2 (m,1H); 3.5–3.65 (m,2H); 2.4–2.7 (m,10H).

Anal. Calcd. for $C_{27}H_{26}F_6N_6OS.0.5\ H_2O$: C, 53.56; H, 4.49; N, 13.88. Found: C, 53.34; H, 4.27; N, 13.74.

EXAMPLE 24

6-[1-[1-[Bis(4-fluorophenyl)methyl]piperazin-4-yl]-2-hydroxy-3-propanylthio]-8-phenylpurine ⅓ Hydrate a. 8-phenyl-6-mercaptopurine.0.25 Hydrate

This procedure is essentially that of A. Herrero et al., Heterocycles, 26, 3123 (1987). To a solution of H₂O (34 mL) and AcOH (7 mL) was added 4,5-diamino-6-mercaptopyrimidine (5.6 mmol, 0.796 g). The mixture was heated until nearly complete dissolution and benzaldehyde (16.8 mmol, 1.7 mL) was added. The mixture was stirred overnight at room temperature. After 24 hr, the mixture was filtered and the precipitate was dissolved in EtOH (2×50 mL) and evaporated (2×) in vacuo to remove the excess aldehyde. The solid was washed with H₂O (2×20 mL) and pentane (3×20 mL) and dried in a vacuum oven at 60° C. overnight to give the pure product as an orange-brown powder (0.53 g, 41.4%), mp. >300° C. DCI/MS (M+1) 229; (300 MHz) ¹H NMR (DMSO-d₆) δ: 13.9 (m,1H); 8.4 (m,2H); 8.2 (s,1H); 7.6 (s,3H).

Anal. Calcd. for $C_{11}H_8N_4S.0.25\ H_2O$: C, 56.76; H, 3.68; N, 24.07. Found: C, 56.90; H, 3.45; N, 23.34.

b. Title compound

To 8-phenyl-6-mercaptopurine (2.2 mmol, 0.5 g) and Et₃N (2.2 mmol, 0.31 mL) in DMF (5 mL) at room temperature was added 1-(1-chloro-2-hydroxy-3-propanyl)-4-(4,4′-difluorobenzhydryl)piperazine (2.2 mmol, 0.84 g) in DMF (15 mL) dropwise over 5 min under nitrogen. After twenty days, the DMF was removed in vacuo (1 mm Hg, 60° C.). Silica gel flash column chromatography using 10% MeOH:CH₂Cl₂ gave the product (950 mg) containing some DMF. Dissolution of the product in CH₂Cl₂ and washing the organic layer with H₂O (2×50 mL) and saturated NaCl (1×50 mL), drying over Na and concentrating in vacuo gave a solid which was dried in a vacuum oven overnight to give the pure product (770 mg, 61.8%), mp 119°–122° C. (dec.). DCI/MS (M+1) 573; (300 MHz) ¹H NMR (CDCl₃) δ: 8.75 (s,1H); 8.25 (m,2H); 7.8 (m,3H); 7.4 (m,4H); 7.0 (m,4H); 4.2 (s,1H); 4.17 (m,1H); 3.6 (m,2H); 2.5 (m,10H).

Anal. Calcd. for $C_{31}H_{30}F_2N_6O.\frac{1}{3}\ H_2O$: C, 64.34; H, 5.34; N, 14.52. Found C, 64.39; H, 5.28; N, 14.10.

EXAMPLE 25

2-Amino-6-[1-[1-[bis(4-fluorophenyl)methyl]piperazin-4-yl]-2-hydroxy-3-propanyl-thio]purine Hemihydrate

To 2-amino-6-mercaptopurine (10 mmol, 1.67 g) in DMF (25 mL) was added triethylamine (10 mmol, 1.4 mL). After stirring about 5 min, 1-(1-chloro-2-hydroxy-3-propanyl)-4-(4,4′-difluorobenzhydryl)piperazine (10 mmol, 3.81 g) in DMF (20 mL) was added dropwise over 5 min. under nitrogen. After one week, the DMF was removed in vacuo and the resultant crude solid was flash chromatographed over silica gel using 5% MeOH:CH₂Cl₂ to give the desired product (2.82 g, 55.1%) as a white solid, mp 118°–122° C. (dec.). MS DCI (M+1) 512; (400 MHz) ¹H NMR (CDCl₃) δ: 7.9 (s, 1H); 7.3 (m, 4H), 6.95 (m, 4H), 4.2 (s, 1H), 4.15 (m, 1H), 3.3 (m, 2H), 2.3–2.6 (m, 10H).

Anal. Calcd. for $C_{25}H_{27}F_2N_7OS.\frac{1}{2}H_2O$: C, 57.68; H, 5.42; N, 18.83. Found: C, 57.48; H, 5.43, N, 18.71.

EXAMPLE 26

6-[1-[1-[Bis(4-fluorophenyl)methyl]piperazin-4-yl-]-2-acetoxy-3-propanylthio]- purin-9-yl-3-propanoic acid, methyl ester

To NaH (0.02 mmol, 0.96 mg, 50% suspension in mineral oil) in DMF (5 mL) at 0° C. was added 6-(1-[1-[bis(4-fluorophenyl)methyl]-piperazin-4-yl]-2-acetoxy-3-propanylthio]purine (1.0 g, 1.8 mmol) neat in portions. After stirring about 15 min, methylacrylate (1.8 mmol, 0.16 mL) was added neat at 0° C. The ice bath was removed and the mixture stirred at room temperature for 7 days. The mixture was then heated on a 60° C. oil bath for 24 h. The DMF was removed in vacuo (1 mmHg, 60° C.) and the crude residue was eluted through silica gel using 10% MeOH:CH₂Cl₂. Pure product was isolated (550 mg, 49.1%) as a glassy solid; mp 55°–58° C. (dec.). DCI/MS (M+1) 625; (300 MHz) ¹H NMR (CDCl₃) δ: 8.15 (s,1H), 8.05 (s,1H), 7.35 (m,4H), 6.95 (m,4H), 5.3 (m,1H), 4.5 (t,2H,J=6.2 Hz), 4.2 (s,1H), 3.4 and 4.0 (q of q 2H), 3.65 (s,3H), 2.91 (t,2H,J=6.1 Hz), 2.6 (d,2H,J=6.1 Hz), 2.55 and 2.35 (m,8H), 2.0 (s,3H).

Anal. Calcd. for $C_{31}H_{34}F_2N_6O_4S$: C, 59.60; H, 5.49; N, 13.45. Found: C, 59.35; H, 5.44; N, 13.33.

EXAMPLE 27

6-[3-[4-[Bis(4-fluorophenyl)methyl]piperazin-1-yl]-2-hydroxy propyl-N-ethylamino]purine a.

1-Ethylamino-3-[4-[bis(4-fluorophenyl)methyl]-1-piperazinyl]-2-propanol.⅛ Hydrate Using ethylamine instead of ammonia in Procedure 18 gives the intermediate as a glass (53%), mp 45°–47° C. IR(neat) 3400–3100, 1604, 1506 cm$^{-1}$; 300 MHz $^1$H NMR (CDCl$_3$) δ: 7.36–6.92 (m, 8H), 4.20 (s, 1H), 3.84 (br m, 1H), 3.0–2.2 (m, 14H), 1.12 (t, 3H); MS 390 (MH+).

Anal. Calcd. for $C_{22}H_{29}F_2N_3O$.⅛ $H_2O$: C, 67.45; H, 7.53; N, 10.73; F, 9.70. Found: C, 67.22; H, 7.60; N, 10.75; F, 9.66.

b. Title compound

Using 1-ethylamino-3-[4-[bis(4-fluorophenyl)methyl]-1-piperazinyl]-2-propanol from above instead of 1-amino-3-[4-[bis(4-fluorophenyl)methyl-1-piperazinyl]-2-propanol in Example 21 gives the product as a colorless solid in 87%, mp 105°–110° C.; IR (KBr) 3400–3100, 1592 cm$^{-1}$; 300 MHz $^1$H NMR (CDCl$_3$) δ: 8.32 (s, 1H), 7.92 (s, 1H), 7.92–6.93 (m, 8H), 4.21 (s, 1H), 3.9–4.27 (br m, 5H), 2.8–2.2 (m,10H), 1.31 (t, 3H); MS 508 (MH+).

Anal. Calcd. for $C_{27}H_{31}F_2N_7O$: C, 63.89; H, 6.16; N, 19.32. Found: C, 63.55; H, 6.06; N, 19.38.

EXAMPLE 28

6-[3-[4-[Bis(4-fluorophenyl)methyl]piperazin-1-yl]-2-hydroxy propyl-N-methylamino]purine Hemihydrate (ORF 25882)

a.

1-Methylamino-3-[4-bis(4-fluorophenyl)methyl]-1-piperazinyl]-2-propanol.¼ Hydrate Using methylamine instead of ammonia in Procedure 18 gives the intermediate as a hygroscopic glass (67%). IR(neat) 3400–3100, 1604, 1506, 1223 cm$^{-1}$; 300 MHz $^1$H NMR (CDCl$_3$) δ: 7.36–6.93(m, 8H), 4.21 (s, 1H), 2.44 (s, 3H), 2.66–2.26 (m, 12H); MS 376 (MH+).

Anal. Calcd. for $C_{21}H_{27}F_2N_3O$.¼ $H_2O$: C, 66.38; H, 7.30; N, 11.06; F, 10.00. Found: C, 66.65; H, 7.34; N, 11.12; F, 10.03.

b. Title compound

Using 1-methylamino-3-[4-[bis(4-fluorophenyl)methyl]-1-piperazinyl]-2-propanol instead of 1-amino-3-[4-bis(4-fluorophenyl)methyl]-1-piperazinyl]-2-propanol in Example 21 gives the product as a colorless glass in 86.5%, mp 100°–115° C.; IR (KBr) 3400–3100, 1592 cm$^{-1}$; 300 MHz $^1$H NMR (CDCl$_3$) δ: 8.35 (s, 1H), 7.92 (s, 1H), 7.35–6.92 (m, 8H), 4.20 (s, 1H), 4.20 (br m, 3H), 3.60 (br m, 3H), 2.61–2.39 (m, 10H); MS 494 (MH+).

Anal. Calcd. for $C_{26}H_{29}F_2N_7O.0.5H_2O$: C, 63.89; H, 6.16; N, 19.32. Found: C, 63.55; H, 6.06; N, 19.38.

EXAMPLE 29

9-Methyl-6-[1-[1-[bis(4-fluorophenyl)methyl]piperazin-4-yl]-2-hydroxy-3- propanylthio]purine Hemihydrate To NaH (5 mmol, 240 mg, 50% in oil, pentane washed and decanted), in DMF (7 mL) was added at −15° C. 6-[1-[1-[bis(4-fluorophenyl)methyl]piperazin-4-yl]-2-hydroxy-3-propanylthio]purine (5 mol, 2.48 g) in DMF (15 mL) over 5 min. After stirring 1 h, methyl iodide (5 mmol, 0.32 mL) in one portion was added at 0° C. under nitrogen. After one hour, the reaction mixture was concentrated under reduced pressure (1 mm Hg, 60° C.) and the crude solid passed through silica gel using 15% MeOH: CH$_2$Cl$_2$ to give the desired product contaminated with DMF. The product was dissolved in CH$_2$Cl$_2$ (50 mL) and washed with H$_2$O (2×50 mL), saturated brine (1×50 mL), dried over Na$_2$SO$_4$ and conconcentrated in vacuo to give pure product (490 mg, 19.2%) as a white glass. mp 68°–70° C. DCI/MS (M+1)=511. (300 MHz) $^1$H NMR (CDCl$_3$) δ: 8.7 (s, 1H), 7.95 (s, 1H), 7.3 (m, 4H), 6.95 (m, 4H), 4.2 (s, 1H), 4.1 (m, 1H), 3.85 (s, 3H), 3.55 (octet, 2H), 2.6 (m, 2H), 2.6 (m, 4H), 2.35 (m, 4H).

Anal. Calc'd for $C_{26}H_{28}F_2N_6OS$.⅛ $H_2O$: C, 60.10; H, 5.62; N, 16.17. Found: C, 59.85, H, 5.34; N, 15.43.

When other alkylating agents such as but not limited to cyclopentyl bromide, cyclohexyl bromide, benzyl chloride, propargyl chloride or allyl chloride are used instead of methyl iodide the corresponding 9-cyclopentyl-, 9-cyclohexyl-, 9-benzyl-, 9-propargyl- or 9-allyl-6-[1-[1-[bis(4-fluorophenyl)methyl]piperazin-4-yl]-2 -hydroxy-3-propanylthio]purine derivatives are obtained.

EXAMPLE 30

2-Methyl-6-[1-[1-[bis(4-fluorophenyl)methyl]piperazin-4-yl]-2-hydroxy-3- propanylthio]purine 3/4 Hydrate To NaH (2.4 mmol, 115 mg, 50% in oil, pentane washed and decanted), in DMF (5 mL) was added 2-methyl-6-mercaptopurine (400 mg, 2.4 mmol) in portions, at 0° C. After stirring 2 h 1-(1-chloro-2-hydroxy-3-propanyl)-4-(4,4′-difluorobenzhydryl)piperazine (2.4 mmol, 0.914 g) was added in DMF (5 mL) dropwise over 15 min, at 0° C., under nitrogen. After three days, the solution was filtered and the DMF removed from the filtrate in vacuo (vacuum oven, 1 mm Hg, 60° C.) to give the crude product. Silica gel flash column chromatography using 10% MeOH:CH$_2$Cl$_2$ gave the product with DMF. This product was dried 72 h in vacuo (room temperature, 1 mm Hg) to give pure product (290 mg, 23.2%). mp 83°–86° C. (dec.) DCI/MS (M+1)=511. (300 MHz) 1H NMR (CDCl$_3$) δ: 8.1 (s, 1H), 7.3 (m, 4H), 6.95 (m, 4H), 4.2 (s, 1H), 4.15 (m, 1H), 3.4 & 3.6 (d of d, 2H), 2.65 (s, 3H), 2.6 (M, 6H), 2.4 (m, 4H).

Anal. Calc'd for $C_{26}H_{28}F_2N_6OS$.¾ $H_2O$: C, 59.57; H, 5.67; N, 16.04. Found: C, 59.47; H, 5.55; N, 16.02.

EXAMPLE 31

6-[1-[1-[Bis(4-methoxyphenyl)methyl]piperazin-4-yl]-2-hydroxy-3-propanylthio]purine 1/5 Hydrate A saturated ethereal hydrochloric acid solution was prepared by treating diethyl ether (100 mL) with concentrated hydrochloric acid (20 mL) and stirring for 45 min. The organic layer was separated and cooled to 0° C. 4-Methoxybenzhydrol (7.4 g, 30 mmol) was added and the mixture was stirred 1 d at room temperature. The ether was removed in vacuo and the residue was dissolved in methylene chloride, dried over sodium sulfate and the solvent was removed in vacuo to give the chloride as an amber oil, 8.2 g, 100%. FAB MS (M+1) 263.

Piperazine (3.9 g, 45 mmol) was dissolved in chloroform (100 mL) containing potassium iodide (2.5 g, 15 mmol) and the solution was treated with the above chloride (4.0 g, 15 mmol) in chlorform (50 mL). The mixture was refluxed for 6 d. Insoluble salts were removed by filtration and the filtrate was concentrated to give a yellow solid, 6.59 g. The solid was dissolved in ether and washed with water (2×100 mL) and saturated brine (1×100 mL) and dried over sodium sulfate. Concentration gave a mixture of starting chloride and alkylated piperazine (3:2) containing approximately 1.1 g (3.5 mmol) of the desired piperazine product.

To this product mixture in ethanol (20 mL) containing sodium bicarbonate (336 mg, 4 mmol) was added epichlorohydrin (0.35 mL, 4.5 mmol) in ethanol (10 mL) dropwise as 0° C. The mixture was stirred for 16 h, the mixture was filtered and the filtrate was concentrated and filtered through silica gel using 2% methanol in methylene chloride to give a 3:1 mixture of product and chloride impurity from the previous reaction (2.0 g, approximately 1.5 g of desired chlorohydrin product).

Sodium hydride (166 mg, 3.5 mmol, prewashed with pentane) in DMF (5 mL) and 6-mercaptopurine (588 mg, 3.5 mmol) were stirred at 0° C. for 1 h. The epichlorhydrin from above (about 1.5 g) in DMF (10 mL) was added at 0° C. and the mixture was stirred for 30 min. The solution was stirred for 6 d at room temperature and the solvent wa removed in vacuo. The residue was purified through silica gel (2×) using 10% methanol in methylene chloride. The pure product was isolated as a solid and dried in vacuo (0.18 g, 10%), mp 110°-113° C., DCI/MS (M+1) 521; (300 MHz) $^1$H NMR (CDCl$_3$) δ: 8.6 (s, 1H), 8.2 (s, 1H), 7.3 (d, 4H), 6.8 (d, 4H), 4.15 (m, 1H), 4.10 (s, 1H), 3.75 (s, 6H), 3.5 & 3.6 (d of d, 2H), 2.75 (m, 2H), 2.4 (m, 4H), 2.3 (m, 4H).

Anal. Calc'd for $C_{27}H_{32}N_6O_3S.1/5\ H_2O$: C, 61.86; H, 6.23; N, 16.03; S, 6.12. Found: C, 61.89; H, 6.23; N, 15.47; S, 5.97.

EXAMPLE 32

2-Chloro-6-[3-[4-Bis(4-fluorophenyl)methyl]piperazin-1-yl]-2-hydroxypropylamino]purine. ¼ Hydrate A mixture of 2,6-dichloropurine (0.945 g, 5 mmol), 1-amino-3-[4-[bis(4-fluorophenyl)methyl]piperazin-1-yl]-2-propanol (1.81 g, 5 mmol) and triethylamine (0.75 mL, 5.4 mmol) was heated to reflux in methanol (25 mL) for 48 h under a nitrogen atmosphere. The solvent was removed in vacuo and the residue was dissolved in methylene chloride and re-evaporated. The solid thus obtained was triturated with water and the product was obtained by filtration and drying as a colorless solid (1.41 g, 555), mp 155°-160° C. $^1$H NMR (CDCl) δ: 7.99 (br s, 1H), 7.33 (m, 46.99 (m, 4H), 4.41 (br s, 1H), 4.33 (s, 1H), 3.69-2.72 (br m, 12H); MS m/z 514 (MH+).

Anal Calc'd for $C_{25}H_{22}ClF_2N_7O.\tfrac{1}{4}\ H_2O$: C, 57.91; H, 5.15; N, 18.91. Found: C, 57.81; H, 4.92; N, 19.18.

CARDIOTONIC ACTIVITY

Adult mongrel dogs were anesthetized with sodium pentobarbital (45 mg/kg, i.p.) and artificially respired. Mean arterial pressure (MAP) was recorded from a Cannulated femoral artery and drugs were infused into a cannulated femoral vein. The arterial pressure pulse was used to trigger a cardiotachometer for determination of heart rate (HR). Left ventricular pressure was measured with a Millar catheter and dP/dt$_{max}$ was derived. A right thoracotomy was performed and myocardial contractile force (CF) was measured with a Walton Brodie strain gauge sutured to the right ventricle. The ventricular muscle was stretched to produce a baseline tension of 100 g. A standard dose of dopamine (10–15 μg/kg/min for 3 min) was administered to determine myocardial responsiveness to ionotropic stimulation.

Test compounds were solubilized in a small volume of DMF diluted to a final concentration of 10% in physiological saline. Alternatively, where possible, a soluble hydrochloride salt was prepared by addition of 0.1N HCl diluted in Physiological saline. Vehicles were tested in appropriate volumes and found to exert less than a 5% effect on contractile force. For iv studies, compounds were administered by infusion pump (one drug per animal) at rates of 0.58–2.2 mL/min in three to four stepwise increasing doses. Each dose was infused over 5 min immediately after the effect of the previous dose peaked. MAP, HR, dP/dt$_{max}$ and CF responses were continuously monitored on a Beckman or Gould recorder and expressed as a percent change from pre-drug control values vs. the cumulative dose of drug administered. For these studies, n represents the number of test animals used.

Quantitation of the ionotropic potency was obtained by calculation of the contractile force (CF) ED$_{50}$. This was defined as the dose of compound that produced a 50% increase above baseline in myocardial contractile force The value was obtained from three to four point dose-response curves using either graphical estimation (n<3) or linear regression analysis (n>3). Data from this evaluation is shown in Table 1. Numbers in parentheses are number of animals screened.

TABLE 1.

| Cardiovascular activity of compounds of the Invention | | | | | |
|---|---|---|---|---|---|
| | | | (% from Control) | | |
| Example | Dose (mg/kg iv) | m | MAP | HR | dPdt | CF |
| 1 | 1.875 (ED$_{50}$ = 0.16 (0.01–0.35)) | 5 | −5 | 1 | 127 | 214 |
| 2 | 1.875 (ED$_{50}$ = 0.07 (0.05–0.09)) | 3 | −13 | −6 | 168 | 212 |
| 3 | 1.875 (ED$_{50}$ = 0.35 (0.23–0.48)) | 3 | −4 | −8 | 91 | 151 |
| 4 | 1.875 | 3 | −12 | −1 | 60 | 86 |
| 5 | 1.875 | 1 | −3 | 5 | 58 | 43 |
| 6 | 1.875 | 1 | 4 | 15 | 80 | 79 |
| 7 | 1.875 | 1 | 1 | 0 | 75 | 97 |
| 7 | 1.875 | 2 | −2 | −4 | 75 | 100 |
| 10 | 1.875 | 1 | 5 | 0 | 47 | 71 |
| 11 | 1.875 (ED$_{50}$ 450 ug/kg) | 2 | −12 | −4 | 62 | 145 |
| 14 | 1.875 | 4 | −6 | 2 | 17 | 38 |
| 15 | 1.875 | 2 | −14 | −7 | 28 | 87 |
| 16 | 1.875 (ED$_{50}$ 608 ug/kg) | 3 | 9 | −4 | 99 | 151 |
| 17 | 1.875 | 1 | −13 | 0 | 16 | 37 |
| 18 | 1.875 (ED$_{50}$ 825 ug/kg) | 2 | 4 | 12 | 58 | 80 |
| 19 | 1.875 | 1 | 2 | 3 | 19 | 43 |
| 20 | 1.875 | 2 | 4 | 2 | 36 | 66 |

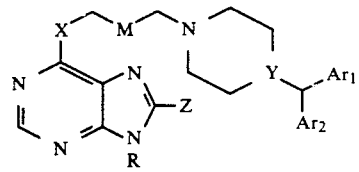

| EX | X | Ar1 | Ar2 | Y | M | Z | R | Dose mpk | MAP | HR | dP/dt | CF |
|---|---|---|---|---|---|---|---|---|---|---|---|---|
| 25 | S | p-FPh | p-FPh | N | CHOH | 2-$NH_2$ | H | 1.875 (1) | −15 | 9 | 23 | 84 |
| 23 | S | m-$CF_3$Ph | m-$CF_3$Ph | N | CHOH | H | H | 1.875 (1) | 7 | −7 | 30 | 44 |
| 24 | S | p-FPh | p-FPh | N | CHOH | 8-Ph | H | 1.875 (2) | −3 | 4 | 5 | 12 |
| 28 | NMe | p-FPh | p-FPh | N | CHOH | H | H | 1.875 (1) | 9 | 16 | 82 | 95 |
| 27 | NEt | p-FPh | p-FPh | N | CHOH | H | H | 1.875 (1) | 3 | 6 | 14 | 10 |
| 26 | S | p-FPh | p-FPh | N | CHOAc | H | $(CH_2)_2CO_2Me$ | 1.875 (2) | −10 | −3 | 29 | 34 |
| 29 | S | p-FPh | p-FPh | N | CHOH | H | Me | 1.875 (2) | −6 | −2 | 11 | 50 |
| 30 | S | p-FPh | p-FPh | N | CHOH | 2-Me | H | 1.875 (2) | 1 | 1 | 17 | 23 |

PROCEDURE 1

3-[4-[Bis(4-fluorophenyl)methyl]-1-piperazinyl]-1,2-propanediol.0.25 Hydrate

To a stirred and warmed solution of 4-fluorobenzhydrylpiperazine (6.343 g, 22 mmol) in MeOH (75 mL), a solution of glycidol (1.63 g, 22 mmol) in MeOH (25 mL) was added slowly under nitrogen The mixture was stirred at room temperature for 18 h, refluxed for 2 h and evaporated to dryness. $CH_2Cl_2$ (4×100 mL) was added to the syrupy residue and the mixture was evaporated to dryness. The syrupy residue was purified by chromatography on a silica gel column (medium pressure). Eluting with 2%-5% MeOH/$CH_2Cl_2$ gave the title compound as a colorless syrup which upon prolonged evacuation formed a hygroscopic foam (5.84 g, 73%), mp 40°–50° C. IR(KBr) $cm^{-1}$: 3625, 3575; $^1$H NMR ($CDCl_3$) δ: 6.9–7.4 (m, 8H, Ar-H); 4.21 [s, 1H, CH(0)2], 3.80 (m, 1H, HCOH), 3.73 and 3.49 (each m, each 1H, $HOCH_2$), 3.8–2.3 (m, 10H, N-CH2); MS(DCI):363 (MH)+.

Anal. Calcd. for $C_{20}H_{24}F_2N_2O_2.\frac{1}{4}H_2O$: C, 65.46; H, 6.73; N, 7.63. Found: C, 65.09; H, 6.66; N, 7.49.

PROCEDURE 2

3-[4-(Diphenylmethyl)-1-piperazinyl]-1,2-propanediol

In a procedure analogous to that of Procedure 1 above, 4-benzyhydrylpiperazine (12.61 g, 0.05 mmol) in MeOH (50 mL) was reacted with glycidol (3.704 g, 0.05 mmol) in MeOH (20 mL) and worked up to give the title compound as a colorless crystalline solid, 13.20 g (81%), mp 130°–131° C. (mp 125–126° C. reported by M. Verderame, J. Med. Chem., 11, 1090 (1968)).

Anal. Calcd for $C_{20}H_{26}N_2O_2$: C, 73.59; H, 8.03; N, 8.58. Found: C, 73.32; H, 8.21; N, 8.48.

PROCEDURE 3

1-(1-Chloro-2-hydroxy-3-porpanyl)-4-[bis(4-fluorophenyl)methyl]piperazine Monohydrate To a mixture of epichlorohydrin (3.5 mL, 0.05 mol) in ethanol (12 mL) at 0° C. (ice bath) and anhydrous $NaHCO_3$ (4.2 g, 0.05 mol) [bis(4-fluorophenyl)methyl]piperazine (14.4 g, 0.05 mol) in ethanol (200 mL) was added dropwise over 45 min under $N_2$. The ice bath was removed and the mixture was allowed to come to room temperature. After 18 h the $NaHCO_3$ was removed by filtration via a sintered glass funnel and the ethanol in the filtrate was removed in vacuo to give the crude product (21.3 g). Silica gel flash chromatography using 2.0% MeOH:$CH_2Cl_2$ gave pure product (10.05 g, 52.9%) as an amber oil. DCI/MS (M+1) 381. 400 MHz $^1$H NMR ($CDCl_3$) δ: 7.3 (m, 4H), 6.95(m, 4H), 4.2 (s, 1H), 3.95 (m, 1H), 3.55 (m, 2H), 2.7 (m, 2H), 2.5 (m, 4H), 2.4 (m, 4H).

Anal. Calcd. for $C_{20}H_{23}ClF_2N_2O.H_2O$: C, 60.22; H, 6.32; N, 7.02. Found: C, 6.29; H, 6.21; N, 6.83.

PROCEDURE 4

1-(1-Chloro-2-hydroxy-3-propanyl)-4-(diphenylmethyl)piperazine

To a mixture of epichlorohydrin (5.1 mL, 0.065 mL) in ethanol (13 mL) and anhydrous $NaHCO_3$ (0.065 mol, 5.46 g) at 0° C., diphenylmethylpiperazine (16.4 g, 0.065 mol) in ethanol (250 mL) was added dropwise over 45 min at room temperature under $N_2$. After 17 h the $NaHCO_3$ was removed by filtration via a sintered glass funnel and the ethanol was removed from the filtrate in vacuo giving a white-yellow solid (21.5 g). This solid after trituration with $Et_2O$ (300 mL) gave a precipitate which was filtered and dried in vacuo to give the pure Product (5.11 g, 22.8 %) mp 114°–116° C. DCI/MS (M+1) 345. 400 MHz $^1$H NMR ($CDCl_3$) δ: 7.2–7.4 (m, 10H), 4.2 (s, 1H), 3.9 (m, 1H), 3.55–3.7 (M, 2H), 2.7 (m, 2H), 2.45 (m, 8H).

Anal. Calcd. for $C_{20}H_{25}ClN_2O$: C, 69.60; H, 7.20; N, 8.10. Found: C, 69.59; H, 7.44; N, 7.96.

PROCEDURE 5

1-(1-Chloro-2-hydroxy-3-propanyl)-4-benzyloioerazine

To a mixture of epichlorohydrin (3.92 mL, 50 mmol) in EtOH (25 mL) and anhydrous $NaHCO_3$ (4.2 g, 50 mmol) 1-benzylpiperazine (8.66 mL, 50 mmol) in EtOH (100 mL) was added dropwise over 30 min at 0° C. under nitrogen. After 16 h the EtOH was removed in vacuo and the crude product was eluted through silica gel (5% MeOH:$CH_2Cl_2$ to give pure product (10.12 g, 75.3%) as an amber oil. DCI/MS (M+1) 269. 400 MHz $^1$H NMR (CDCl ) δ: 7.3 (m, 5H), 4.95 (m, 1H), 4.5 & 4.6 (m, 2H), 3.95 (m, 1H), 3.6 (m, 2H), 3.5 (s, 2H), 2.7 (m, 4H), 2.4 (m, 4H).

Anal. Calcd. for $C_{14}H_{21}ClN_2O$: C, 62.50; H, 7.87; N, 10.40. Found: C, 62.41; H, 7.83; H, 10.35.

PROCEDURE 6

1-(1-Chloro-2-hydroxy-3-propanyl)-4-piperonylpiperazine

To a mixture of epichlorohydrin (3.9 mL, 50 mmol) in EtOH (25 mL) and anhydrous NaHCO$_3$ (4.2 g, 50 mmol) 1-piperonylpiperazine (11.0 g, 50 mmol) in EtOH (125 mL) was added dropwise over 45 min at 0° C., under nitrogen. After 16 h and removal of the EtOH in vacuo. the crude material was passed through silica gel (vacuum, 5% MeOH:CH$_2$Cl$_2$) to give pure product (3.85 g, 26.4%) as an amber oil DCI/MS (M+1) 313. 400 MHz $^1$H NMR (CDCl$_3$) δ: 7.25 (s, 1H), 6.7–6.8 (m, 2H), 5.9 (s, 2H), 4.6 (m, 1H), 3.9 (m, 1H), 3.5 (m, 2H), 3.4 (s, 2H), 2.4–2.7 (m, 10H).

Anal. Calcd. for C$_{15}$H$_{21}$N$_2$O$_3$Cl: C, 57.59; H, 6.77; N, 8.95. Found: C, 57.24; H, 6.84; N, 8.73.

PROCEDURE 7

1-(1-Chloro-2-hydroxy-3 propanyl)-4-(4-chlorobenzhydryl)piperazine Hemihydrate To a mixture of epichlorohydrin (3.92 mL, 50 mmol) in ethanol (25 mL) and NaHCO$_3$ (4.2 g, 50 mmol) 4-chlorobenzhydryl piperazine (14.34 g, 50 mmol) in EtOH (150 mL) was added dropwise over 45 min at 0° C. under nitrogen. After 20 h, the EtOH was removed in vacuo and the residue was eluted through silica gel using 50% MeOH:CH$_2$Cl$_2$ to give the pure product (3.40 g, 18.3%) as a white solid, mp 72°–74° C. DCI/MS (M+1) 379; 400 MHz $^1$H NMR (CDCl ) δ: 7.5–7.35 (m, 9H), 4.2 (s, 1H), 3.65 (m, 2H), 2.9 (m, 2H), 2.7–2.6 (m, 8H).

Anal Calcd. for C$_{20}$H$_{24}$Cl$_2$N$_2$O.½H$_2$O: C, 61.80; H, 6.44; N, 7.20. Found: C, 61.67; H, 6.37; N, 7.10.

PROCEDURE 8

1-(1-Chloro-2-hydroxy-3-propanyl)-4-bis(4-chlorophenyl)methyl]piperazine 4,4'-Dichlorobenzhydrylpiperazine (6.0 g, 18.7 mmol) was reacted as above with epichlorohydrin to give the title compound as an amber oil, 3.67 g (49.8%). 100 MHz $^1$H NMR (CDCl$_3$) δ: 7.3 (s, 8H), 4.2 (s, 1H), 3.9 (m, 1H), 3.6 (d, 2H, J=10 Hz), 2.9 (m, 2H), 2.7–2.4 (m, 10H).

PROCEDURE 9

1-(1-Chloro-2-hydroxy-3-propoxyl-4-carbethoxvoioerazine.Hemihydrate

Carbethoxypiperazine (7.28 mL, 50 mmol) was reacted as above with epichlorohydrin to give the title compound as a clear oil, 8.69 g (69.3%). DCI/MS (M+1) 251; 400 MHz $^1$H NMR (CDCl$_3$) δ: 4.15 (q, 2H, J=7.1 Hz), 3.9 (m, 1H), 3.6 (m, 2H), 3.5 (m, 4H), 2.6–2.4 (m, 4H), 2.5 (d, 2H, J=6.5 Hz), 1.25 (t, 3H, J=7.11 Hz).

Anal. Calcd. for C$_{10}$H$_{19}$ClN$_2$O$_3$.½H$_2$O: C, 46.24; H, 7.76; N, 10.78. Found: C, 46.58; H, 7.47; N, 10.65.

PROCEDURE 10

1-(1-Chloro-2-hydroxy-3-propanyl)-4-[bis(3,4'-trifluoromethylphenyl)methyl]piperazine.5/4 Hydrate 3,4'-Trifluoromethylphenylpiperazine (1.7 g, 4.4 mmol) was reacted as above with epichlorohydrin to give the title compound as an amber oil, 1.23 g (72%). DCI/MS (M+1) 481; 400 MHz $^1$H NMR (CDCl$_3$) 67 : 7.68 (s, 1H), 7.6–7.4 (m, 7H), 4.39 (s, 1H), 3.9 (m, 1H), 3.55 (m, 2H), 2.7 (m, 2H), 2.55–2.4 (m, 8H).

Anal. Calcd. for C$_{22}$H$_{23}$ClF$_6$N$_2$O.5/4H$_2$O: C, 52.54; H, 5.11; N, 5.57. Found: C, 52.48; H, 5.41; N, 5.22.

PROCEDURE 11

1-(1-Chloro-2-hydroxy-3-propanyl)-4-(triphenylmethyl)piperazine.¼ Hydrate 1-(Triphenylmethyl)piperazine (5.25 g, 16 mmol) was reacted as above with epichlorohydrin to give the title compound as a white solid, 2.79 g (41.4%), mp 91°–94° C. DCI/MS (M+1) 421; 400 MHz $^1$H NMR (CDCl$_3$) δ: 7.5–7.15 (m, 15H), 3.86 (m, 1H), 3.52 (d, 2H, J=4.85 Hz), 2.9 (m, 2H), 2.8–2.4 (m, 10H).

Anal. Calcd. for C$_{26}$H$_{29}$ClN$_2$O.¼H$_2$O: C, 73.39; H, 6.99; N, 6.58. Found: C, 73.34; H, 6.83; N, 6.53.

PROCEDURE 12

1-[Bis(4-chlorophenyl)methyl]piperazine

To 4-chlorobenzhydrol (12.66 g, 50 mmol) in CH$_2$Cl$_2$ (200 mL) under nitrogen, thionyl chloride (10 mL, 137 mmol) was added dropwise over 15 min. After 18 h and removal of the solvent in vacuo, the crude product was dissolved in CH$_2$Cl$_2$ (100 mL) and washed with saturated NaHCO$_3$ (3×), dried over Na , and concentrated in vacuo to a thin, amber oil (12.53 g). Upon standing at room temperature for 1 h, crystallization occured to give pure Product (12.5 g, 88.4%) as a white solid, mp 61°–64° C. DCI/MS (M+1) 235. 400 MHz $^1$H NMR (CDCl$_3$) δ: 7.35 (m, 8H), 6.05 (s, 1H).

Anal. Calcd. for C$_{13}$H$_9$C$_{13}$: C, 57.49; H, 3.34. Found: C, 57.69; H, 3.46.

This is a known compound: *Chem. Abstract.*. 1957, 1, 9717a.

To piperazine (9.15 g, 106 mmol) in CHCl$_3$ (200 mL) containing potassium iodide (2.66 g, 16 mmol) under a nitrogen atmosphere bis(4-chlorophenyl)chloromethane (9.5 g, 35 mmol) in CHC$_3$ (100 mL) was added dropwise with stirring over a period of 45 min. After 6 days, the reaction mixture was filtered, concentrated and the crude product was purified by flash chromatography using 10% MeOH in CH$_2$Cl$_2$ to give the title compound as a thick amber oil. 400 MHz $^1$H NMR (CDCl$_3$) δ: 7.25 (m,8H), 4.25 (s,1H), 2.9 (m, 4H), 2.3 (m, 4H).

PROCEDURE 13

(2S)-(−)-(1.2-Epoxypropyl)-4-[bis(4-fluorophenyl)methyl]piperazine.¼ Hydrate To NaH (0.9 g, 18.75 mmol, 50% suspension in mineral oil) previously washed with pentane in DMF (8 mL) 4,4'-difluorobenzhydrylpiperazine (5.0 q, 17.4 mmol) in DMF (15 mL) was added dropwise under nitrogen over 15 min at 0° C. After 15 min at 0° C., the mixture was warmed to room temperature. After 2 h the mixture was cooled to 0° C., (2R)-(−)-glycidyl tosylate (4.0 g, 17.5 mmol) in DMF (16 mL) was added dropwise and the mixture was stirred at room temperature for 24 h under nitrogen. After filtration through celite, the mixture was concentrated in vacuo (1 mmHg, 55° C.) and the residue was dissolved in CH$_2$Cl$_2$. Refiltration of the solution, concentration and flash chromatography of the resultant oil through silica gel using 10% MeOH: CH$_2$Cl$_2$ gave the title compound as an amber oil, 4.66 g (82.6%); DCI/MS (M+1) 345; 400 MHz $^1$H NMR (CDCl$_3$) δ: 7.4 (m, 4H), 7.0 (m, 4H), 4.25 (s, 1H), 3.1 (m, 1H), 2.8 (m, 2H), 2.7–2.4 (m, 8H), 2.3 (m, 2H); $[\delta]_D^{22}$ −7.5° (0.5% in EtOH).

Anal. Calc'd for $C_{20}H_{22}F_2N_2O \cdot \frac{1}{4}H_2O$: C, 68.89; H, 6.50; N, 8.03. Found: C, 69.17; H, 6.53; N, 8.02.

PROCEDURE 14

(2R)-(+)-(1,2-Epoxypropyl)-4-[bis(4-fluorophenyl)methyl]piperazine Hydrate

Using a similar procedure to that described above, (2S)-(+)-glycidyl tosylate (2.0 g, 8.76 mmol) was used to prepare the title compound as an amber oil, 2.57 g (77.8%); DCI/MS (M+1) 345; 400 MHz $^1$H NMR (CDCl$_3$) δ: 7.35 (m, 4H), 6.95 (m, 4H), 4.2 (s, 1H), 3.1 (m, 1H), 2.55 (m, 2H), 2.45–2.3 (m, 8H), 2.2 (m, 2H); $[\delta]_D^{22}$ +7.2° (0.5% in EtOH).

Anal. Calc'd for $C_{20}H_{22}F_2N_2O \cdot H_2O$: C, 66.68; H, 6.67; N, 7.73. Found: C, 66.51; H, 6.38; N, 7.73.

PROCEDURE 15

6-Chloro-9-(tetrahydro-2-pyranyl)purine

To a warmed (60° C.) slurry of 6-chloropurine (20 g, 0.1294 mol) and p-toluenesulfonic acid monohydrate (0.35 g), dihydropyran (13.4 mL, 0.172 mol) was added with stirring over a period of 30 min. After an additional 30 min of heating, the mixture was allowed to cool to room temperature for 1 h. Concentrated ammonium hydroxide (12 mL) was added and stirring was continued for 5 min. The solution was washed with water (4×70 mL) and the organic layer was dried (Na$_2$SO$_4$), filtered and concentrated in vacuo to give a syrup (about 29 g) which slowly crystallized upon standing. Extraction with boiling hexane gave the product as a solid, 24.36 g in two crops (78%), mp 70°–71° C.

Anal. Calcd for $C_{10}H_{11}ClN_4O$: C, 50.32; H, 4.65; N, 23.47. Found: C, 50.25; H, 4.59; N, 23.25.

This is a known compound: R. K. Robins et al., *J. Amer. Chem. Soc.*, 83, 2574 (1961).

PROCEDURE 16

1-(1-Chloro-3-propanyl)-4-[bis(4-fluorophenyl)methyl]piperazine

Pentane (10 mL) was added to sodium hydride (0.50 g, 11 mmol of 50% suspension in mineral oil) and the mixture was stirred under nitrogen. The pentane was decanted. Anhydrous DMF (12 mL) was added and the suspension was cooled to 0° C. [Bis(4-fluorophenyl)methylpiperazine (2.9 g, 10 mmol) in anhydrous DMF (14 mL) was added at 0° C. within 10 min. The reaction mixture was allowed to warm to room temperature. After 1 h, the mixture was cooled to 0° C. and to the light green solution 1-chloro-3-bromopropane (5 mL, 50 mmol) in anhydrous DMF (5 mL) was added over a period of 10 min. The mixture was stirred under nitrogen at room temperature for 72 h. The solvents were evaporated in vacuo (1 mm Hg) at 50° C. The residue was triturated in methylene chloride and filtered through celite. The filtrate was washed with water (2×100 mL), dried (sodium sulfate), filtered, and the filtrate was evaporated in vacuo to give crude chloropropyl compound (3.65 g). Pentane (50 mL) was added, and on the next day the pentane insoluble solid was removed by filtration. The filtrate was evaporated in vacuo to give the title compound (2.3 g, 75%) as a clear, colorless oil. 100 MHz $^1$H NMR (CDCl$_3$) δ: 7.32 (m, 4H), 6.95 (m, 4H), 4.2 (s, 1H), 3.57 (m, 2H), 2.2–2.6 (m, 10H), 1.9 (m, 2H). DCI/MS (M+1) 361.

Anal. Calcd. for $C_{20}H_{23}ClF_2N_2$: C, 65.83; H, 6.35; N, 7.68. Found: C, 65.59; H, 6.42; N, 7.63.

PROCEDURE 17

1-[1-(2,3-Epoxy)propyl]-4-[bis(4-fluorophenyl)methyl]piperazine

A solution of 4,4'-difluorobenzhydrylpiperazine (28.83 g, 100 mmol) in acetonitrile (250 mL) was added to an ice cold mixture of epibromohydrin (9.1 mL, 110 mmol) and anhydrous potassium carbonate (15.2 g, 110 mmol) in acetonitrile (150 mL) over a period of 40 min. The mixture was stirred at room temperature for 100 h, filtered and the solids were washed with methylene chloride. The combined filtrates were concentrated to dryness to give an oil which was eluted through a flash chromatographic silica gel column using 2–3% methanol/methylene chloride to give the title compound as glass, 23.98 (69.6); 300 MHz $^1$H NMR (CDCl$_3$) δ: 4–6.9 (m, 8H). 4.22 (s. 1H). 3.09 (br m, 1H), 2.8–2.25 (m, 12H); MS 345 (MH+).

Anal. Calcd. for $C_{20}H_{22}F_2N_2O$: C, 69.75; H, 6.44; N, 8.13; F, 11.50. Found: C, 69.73; H, 6.49; N, 8.19; F. 11.66.

PROCEDURE 18

1-Amino-3-4-[bis(4-fluorophenyl)methyl]-1-piperazinyl]-2-propanol

A solution of 1-[1-(2,3-epoxy)propyl]-4-[bis-(4-fluorophenyl)methyl] piperazine (8.9 g, 25.8 mmol) and liquid ammonia (20 mL) in EtOH (40 mL) was heated in a teflon reaction vessel in a bomb at 110° C. for 28 h. The solution was then evaporated to dryness to give about 10 g of a glass which was purified using flash chromatography on silica gel and increasing proportions of methanol in methylene chloride to give the product as an oil which solidified upon vacuum drying, 5.7 g (61%), mp 45°–47° C. IR(neat) 3350 cm$^{-1}$; 300 MHz IH NMR (CDCl$_3$) δ: 7.4–6.9 (m, 8H), 4.21 (s, IH), 3.68 (br m, IH) 2.8–2.2 (m,12H); MS 362 (MH+).

Anal. Calcd. for $C_{20}H_{25}F_2N_3O$: C, 66.46; H, 6.97; N, 11.63. Found; C, 66.21; H, 7.10; N, 11.63.

PROCEDURE 19

2-Methylhypoxanthine

A solid mix of 4-amino-5-imidazolecarboxamide hydrochloride (30.75 mmol, 5 g) and acetamidine hydrochloride (2 eq, 61.5 mmol, 5.8 g) and sodium acetate (3 eq, 92.25 mmol, 7.6 g) were heated at 190° C. for 1 h. To the resultant off-white solid, at RT, NaOH (100 ml) was added and a white ppt was filtered away. The filtrate was acidified to pH 6.0 with AcOH (5 ml) and the resultant ppt filtered away. Both precipitates were dried separately in a vacuum oven at 0° C. for 24 h. The combined weight of pure product was (4.16 g, 90%). The first precipitate (2.11 g) analyzed as follows: mp.>300° C. DCI/MS (M+1)=151. (300 MHz) $^1$H-nmr (DMSO-d$_6$) δ: 8.0 (s, 1H), 2.3 (s, 3H).

Anal. Calcd. for $C_6H_6N_4O$: C, 48.00; H, 4.03; N, 37.32. Found: C, 47.20; H, 3.91; N, 37.36.

PROCEDURE 20

2-Methyl-6-mercaptopurine

To 2-Methylhypoxanthine (1.3 g, 8.6 mmol) and P$_2$S$_5$ (5 g) was added pyridine (50 mL). The mixture was refluxed for 4 h. The pyridine was distilled away and NaOH (50 mL) was added to the residue. A brown precipitate was filtered away. The precipitate was dried in a vacuum oven at 80° C. for 24 h to give the desired product (.77 g, 46.3%) as a light brown solid. mp>300° C. DCI/MC (M+1)=167. (300 MHz) $^1$H-nmr (DMSO-d$^6$) δ: 8.3 (s, 1H), 2.45 (s, 3H).

Anal. Calcd. for $C_6H_6N_4.\frac{1}{3} H_2O$: C, 42.85; H, 3.90; N, 32,53. Found: C, 42.02; H, 3.47; N, 31.93.

PROCEDURE 21

8-Phenyl-6-mercaptopurine.0.25 Hydrate

To a solution of H$_2$O (34 mL) and AcOH (7 mL) was added 4,5-diamino-6-mercaptopyrimidine (5.6 mmol, 0.796 g). The mixture was heated until nearly complete dissolution. Benzaldehyde (16.8 mmol, 1.7 mL) was added and the mixture was stirred overnight at RT. After 24 hr. the mixture was filtered and the collected precipitate was dissolved in EtOH (2×50 mL) and evaporated (2x) in vacuo to remove the excess aldehyde. The solid was washed with H$_2$O (2×20 mL) and pentane (3×20 mL) and dried in a vacuum oven at 60° C. overnight to give the pure product as an orange-brown powder (0.53 g, 41.4%), mp. >300° C. DCI/MS M+1 229; (300 MHz) $^1$Hnmr (DMSO-d$_6$) δ: 13.9 (m, 1H); 8.4 (m,2H); 8.2 (s,1H); 7.6 (s,3H).

Anal. Calcd. for $C_{11}H_8N_4S.0.25H_2O$: C, 56.76; H, 3.68; N, 24.07. Found: C, 56.90; H, 3.45; N, 23.34.

PROCEDURE 22

1-(1-Chloro-2-hydroxy-3-propanyl)-4-(3.4'-trifluoromethyl) phenylmethyl]piperazine Hemihydrate To epichlorohydrin (5 mmol, 0.4 mL) and NaHCO$_3$ (5 mmol, 0.420 g) in ethanol (5 mL) was added at 0° C. [3,3'-trifluoromethyl)phenyl]phenyl]piperazine (1.96 g, 5 mmol) in ethanol (25 mL) dropwise over 10 min under nitrogen. After 20 hours, the NaHC$_3$ was filtered away and the ethanol removed in vacuo to give the crude product. Silica gel flash column chromatography using 5% MeOH:CH$_2$Cl$_2$ gave the desired product (2.16 g, 90.0%) as a clear oil. DCI/MS M+1 481.

PROCEDURE 23

1-Ethylamino-3-[4-[bis(4-fluorophenyl)methyl]-1-piperazinyl]-2-propanol.⅛ Hydrate Using ethylamine instead of ammonia in Procedure 18 gives the title compound as a glass (53%), mp 45°-47° C. IR(neat) 3400-3100, 1604, 1506 cm−$^1$; 300 MHz $^1$H NMR (CDCl$_3$) δ: 7.36-6.92 (m,8H), 4.20 (s,1H), 3.84 (br m, 1H), 3.0-2.2 (m, 14H), 1.12 (t, 3H); MS 390 (MH+).

Anal. Calcd. for $C_{22}H_{29}F_2N_3O.\frac{1}{8}H_2O$: C, 67.45; H, 7.53; N, 10.73; F, 9.70. Found: C, 67.22; H, 7.60; N, 10.75; F, 9.66.

PROCEDURE 24

1-Methylamino-3-4-[bis(4-fluorophenyl)methyl]-1-piperazinyl]-2-propanol.¼ Hydrate Using methylamine instead of ammonia in Procedure 18 gives the title compound as a hygroscopic glass (67%). IR)neat) 3400-3100, 1604,1506, 1223 cm−$^1$; 300 MHz $^1$H NMR (CDCl$_3$) δ: 7.36-6.93 (m, 8H), 4.21 (s,1H), 2.44 (s,3H), 2.66-2.26 (m, 12H); MS 376 (MH+).

Anal Calcd. for $C_{21}H_{27}F_2N_3O.\frac{1}{4} H_2O$: C, 66.38; H, 7.30; N, 11.06; F, 10.00. Found: C, 66.65; H, 7.34; N, 11.12; F, 10.03.

What is claimed is:

1. A compound selected from the group consisting of:
  6-[1-[1-[bis(3-trifluoromethylphenyl)methyl]piperazin-4-yl]-2-hydroxy-3-propanylthio]purine,
  6-[1-[1-[bis(4-fluorophenyl)methyl]piperazin-4-yl]-2-hydroxy-3-propanylthio]-8-phenylpurine,
  2-amino-6-[1-[1-[bis(4-fluorophenyl)methyl]piperazin-4-yl]-2-hydroxy-3-propanyl-thio]purine, and
  6-[1-[1-[bis(4-fluorophenyl)methyl]piperazin-4-yl-]-2-acetoxy-3-propanylthio]purin-9-yl-3-propanoic acid, methyl ester.

2. A compound selected from the group consisting of:
  6-[3-[4-[bis(4-fluorophenylmethyl]piperazine-1-yl]-2-hydroxypropyl-N-ethylamino]purine,
  6-[3-[4-bis(4-fluorophenyl)methyl]piperazin-1-yl]-2-hydroxypropyl-N-methylamino]purine, and
  9-methyl-6-[1-[1-bis(4-fluorophenyl)methyl]piperazin-4-yl]-2-hydroxy-3-propanylthio]purine.

3. A compound selected from the group consisting of:
  2-methyl-6-[1-[1-[bis(4-fluorophenyl)methyl]piperazin-4-yl]-2-hydroxy-3-propanylthio]purine,
  6-[1-[1-[bis(4-methoxyphenyl)methyl]piperazin-4-yl]-2-hydroxy-3-propanylthio]purine, and
  2-chloro-6-[3-[4-[bis(4-fluorophenyl)methyl]piperazin-1-yl]-2-hydroxypropylamino]purine.

4. A compound is 6-[3-[4-[bis(4-fluorophenyl)methyl]piperazin-1-yl]-2-hydroxypropylamino]purine.

* * * * *